US008642836B2

(12) United States Patent
Hawkes et al.

(10) Patent No.: US 8,642,836 B2
(45) Date of Patent: *Feb. 4, 2014

(54) METHOD OF SELECTIVELY PRODUCING MALE OR FEMALE STERILE PLANTS

(75) Inventors: Timothy Robert Hawkes, Bracknell (GB); Glynn Mitchell, Bracknell (GB); Stephen Thomas Hadfield, Bracknell (GB); Paul Anthony Thompson, Bracknell (GB); Russell Viner, Bracknell (GB); Yan Zhang, Apex, NC (US)

(73) Assignee: Syngenta Limited, Guildford, Surrey (GB)

( * ) Notice: Subject to any disclaimer, the term of this patent is extended or adjusted under 35 U.S.C. 154(b) by 1194 days.

This patent is subject to a terminal disclaimer.

(21) Appl. No.: 12/111,364

(22) Filed: Apr. 29, 2008

(65) Prior Publication Data

US 2008/0250535 A1    Oct. 9, 2008

Related U.S. Application Data

(62) Division of application No. 10/504,784, filed as application No. PCT/GB03/00683 on Feb. 14, 2003.

(30) Foreign Application Priority Data

Feb. 26, 2002 (GB) .................................. 0204484.0
Oct. 8, 2002 (GB) .................................. 0223359.1

(51) Int. Cl.
*A01H 1/00* (2006.01)
*A01H 5/00* (2006.01)
*C12N 15/82* (2006.01)
*C07H 21/04* (2006.01)

(52) U.S. Cl.
USPC ........ 800/274; 800/303; 800/278; 536/23.74; 536/23.2

(58) Field of Classification Search
USPC ....................................................... 800/274
See application file for complete search history.

(56) References Cited

U.S. PATENT DOCUMENTS

| | | | |
|---|---|---|---|
| 4,810,648 A | 3/1989 | Stalker | |
| 5,153,355 A | 10/1992 | Mildenberger et al. | |
| 5,254,801 A | 10/1993 | Dotson et al. | |
| 5,347,047 A | 9/1994 | Siegel et al. | |
| 5,470,359 A | 11/1995 | Huffman | |
| 5,510,471 A | 4/1996 | Lebrun et al. | |
| 5,543,306 A | 8/1996 | Pohlenz et al. | |
| 5,639,948 A | 6/1997 | Michiels et al. | |
| 5,767,378 A | 6/1998 | Bojsen et al. | |
| 7,105,349 B2 * | 9/2006 | Nasholm et al. | 435/468 |
| 7,939,709 B2 * | 5/2011 | Hawkes et al. | 800/274 |

FOREIGN PATENT DOCUMENTS

| | | |
|---|---|---|
| EP | 0242246 | 10/1987 |
| EP | 0257542 | 3/1988 |
| EP | 0360750 | 3/1990 |
| EP | 0412006 | 2/1991 |
| EP | 0690133 | 1/1996 |
| EP | 1481068 | 2/2011 |
| FR | 2673673 | 9/1992 |
| GB | 0204484 | 2/2002 |
| GB | 0223359 | 10/2002 |
| WO | WO 92/04449 | 3/1992 |
| WO | WO 92/04454 | 3/1992 |
| WO | WO 92/13956 | 8/1992 |
| WO | WO 94/01560 | 1/1994 |
| WO | WO 96/26283 | 8/1996 |
| WO | WO 98/13504 | 4/1998 |
| WO | WO 98/39462 | 9/1998 |
| WO | WO 98/48023 | 10/1998 |
| WO | WO 98/56238 | 12/1998 |
| WO | WO 99/42598 | 8/1999 |
| WO | WO 99/46396 | 9/1999 |
| WO | WO 99/48023 | 9/1999 |
| WO | WO 00/61740 | 10/2000 |
| WO | WO 00/66748 | 11/2000 |
| WO | WO 01/29237 | 4/2001 |
| WO | WO 03/60133 | 7/2003 |
| WO | WO 03/72792 | 9/2003 |

OTHER PUBLICATIONS

Angenent et al., The Plant Cell, 7, 1569-1582, 1995.
Baulcombe et al., Nature, 321, 446-449, 1986.
Bayley et al., Plant Molecular Biology, 18, 353-361, 1992.
Beeson et al., Journal of Chromatography, 634, 2, 197-204, 1993.
Bevan et al., Nucleic Acids Research, 12, 22, 8711-8721, 1984.
Bewick et al., Pesticide Science, 17, 349-356, 1989.
Bhushan et al., Biomedical Chromatography, 12, 6, 309-316, 1998.

(Continued)

*Primary Examiner* — Li Zheng

(74) *Attorney, Agent, or Firm* — Yoshimi D. Barron

(57) ABSTRACT

A method of producing male or female sterile plants comprising the steps of transforming plant material with a polynucleotide which encodes at least one enzyme which reacts with a non-phytotoxic substance to produce a phytotoxic one, and regenerating the thus transformed material into a plant, wherein the said non-phytotoxic substance is applied to the plant up to the time of male or female gamete formation and/or maturation, so that the non-phytotoxic substance provides for the production of a phytotoxic one which selectively prevents the formation of or otherwise renders the said gametes non-functional, wherein the enzyme is expressed preferentially in either male or female reproductive structures, characterized in that (i) the non-phytotoxic substance is a D-alpha amino acid, and (ii) the enzyme is a D-amino acid oxidase.

24 Claims, 2 Drawing Sheets

(56) References Cited

OTHER PUBLICATIONS

Dotson et al., The Plant Journal, 10, 383-392, 1996.
Dzelzkalns et al., The Plant Cell, 5, 855-863, 1993.
Gabler et al., Enzyme and Microbial Technology, 27, 8, 605-611, 2000.
Gallie et al., Nucleic Acids Research, 15, 8693-8711, 1987.
Goldman et al., The EMBO Journal, 13, 2976-2984, 1994.
Gritz et al., Gene, 25, 179-188, 1983.
Guerrero et al., Molecular and General Genetics, 224, 161-168, 1990.
Hamilton et al., Sexual Plant Reproduction, 2, 208-212, 1989.
Haslam et al., Pesticide Biochemistry and Physiology, 71, 3, 178-189, 2001.
Horsch et al., Science, 227, 1229-1231, 1985.
Jeon et al., Plant Molecular Biology, 39, 35-44, 1999.
Johannsen et al., Journal of Chromatography, 937, 1-2, 135-138, 2001.
Klee et al., Molecular and General Genetics, 210, 437-443, 1987.
Kriete et al., The Plant Journal, 9, 809-818, 1996.
Lyznik et al., Nucleic Acids Research, 24, 3784-3789, 1996.
Menzel-Soglowek et al., Journal of Chromatography, 532, 295-303, 1990.
Meyer et al., Nature, 330, 677-678, 1987.
Mutsaers et al., Recueil des Travaux Chimiques des Pays-Bas, 110, 5, 185-188, 1991.
Nadeau et al., The Plant Cell, 8, 213-239, 1996.
Rothstein et al., Gene, 53, 153-161, 1987.
Savidge et al., The Plant Cell, 7, 721-733, 1995.
Shieh et al., Journal of Biological Chemistry, 268, 3487-3493, 1993.
Skuzeski et al., Plant Molecular Biology, 15, 65-79, 1990.
Spena et al., Theoretical and Applied Genetics, 84, 520-527, 1992.
Theissen et al., Gene, 156, 155-166, 1995.
Twell et al., Development, 109, 705-713, 1990.
Wakeley et al., Plant Molecular Biology, 37, 187-192, 1998.
Wright et al., The Plant Journal, 3, 1, 41-49, 1993.
Zu et al., Proceedings of the National Academy of Sciences of the United States of America, 92, 2106-2110, 1995.
Scheid, Nature Biotechnology, 22, 4, 398-399, 2004.
Kano-Murakami et al., FEBS, 334, 3, 365-368, 1993.
Pilone, M.S., D-amino acid oxidase: new findings, Cell. Mol. Life Sci, 2000, pp. 1732-1747, vol. 57.
Robinson, T. D-amino acids in higher plants, Life Sciences, 1976, pp. 1097-1102, vol. 19.
Wilson, D.G., King, K.W., and Burris, R.H., Transamination reactions in plants, JBC, 1954, pp. 863-874.
Hoerlein, T., Glufosinate (phosphinothricin), a natural amino acid with unexpected herbicidal properties, Rev Environ Contam Toxicol, 1994, pp. 73-145, vol. 138.
Pollegioni, L., Falbo, A. and Pilone, M. Specificity and kinetics of *Rhodotorula gracilis* D-amino acid oxidase, Biochimica et Biophysica Acta, 1992, pp. 11-16, vol. 1120.
Pollegioni, L. et al., M. Studies on the structural and functional aspects of *Rhodotorula gracilis* D-amino acid oxidase . . . , Biochem. J., 1995, pp. 577-58, vol. 310.
Aldag, R.W., and Young, J.L., D-amino acids in soils. I. Uptake and metabolism by seedling maize and ryegrass, Agronomy Journal, 1970, pp. 184-189, vol. 62(2).
Borstlap, A.C., Interactions between the branched-chain amino acids in the growth of *Spirodela polyrhiza*, Planta, 1981, pp. 314-319, vol. 151.
Gamburg, K.Z., and Rekoslavskaya, N.L., Formation and functions of D-amino acids in plants, Fiziologiya Rastenii, 1991, pp. 1236-1246, vol. 38.
Manabe, H. and Ohira, K., Effects of D- and L-alanine on the growth of suspension-cultured rice, soybean and tobacco cells, Soil Sci Plant Nutr, 1981, pp. 383-386, vol. 27(3).
Ruhland, M.et al., A comparative investigation of the metabolism of the herbicide glufosinate . . . , Environ. Biosafety Res., 2002, pp. 29-37, vol. 1.
Sacchi, S. et al., Engineering the substrate specificity of D-amino-acid oxidase, The Journal of Biological Chemistry, 2002, pp. 27510-27516, vol. 277(30).
Hawkes, T. et al., D-glufosinate as a male sterility agent for hybrid seed production, Plant Biotechnology Journal, 2011, pp. 301-314, vol. 9.
Bosacchi, M, Selective plant growth using D-amino acids, Master Thesis Submitted at The State University of New Jersey, May 2008, pp. i-46.
Umhau, S. et al., The x-ray structure of D-amino acid oxidase at very high resolution . . . , PNAS, 2000, pp. 12463-12468, vol. 97(23).
Zeiss, H., Recent advances in the stereoselective synthesis of L-phosphinothricin, Pestic, Sci., 1994, pp. 269-277, vol. 41.
Pollegioni, L. et al., Kinetic mechanism of D-amino acid oxidases from *Rhodotorula gracilis* and *Trigonopsis variabilis*, J Biol Chem., 1993, pp. 13850-13857, vol. 268(19).
Erikson, O. et al., A conditional marker gene allowing both positive and negative selection in plants, Nature Biotechnology, 2004, pp. 455-458, vol. 22(4).

\* cited by examiner

METHOD OF SELECTIVELY PRODUCING MALE OR FEMALE STERILE PLANTS

This is a divisional application of U.S. application Ser. No. 10/504,784, filed Feb. 25, 2005, a national stage application under 35 U.S.C. §371 of International Application No. PCT/GB03/00683, filed on Feb. 14, 2003, which is entitled to the benefit of Great Britain Application No. 0204484.0, filed on Feb. 26, 2002 and Great Britain Application No. 0223359.1, filed on Oct. 8, 2003, which are incorporated by reference in their entireties.

Heterosis in crop plants can have a marked effect on yield improvement. In general, hybrids exhibit increased yields in comparison with non-hybrid varieties. Hybrids usually give a greater return unit for growth factors such as water and fertilizer. Hybrids often offer superior stress tolerance, uniformity in product and maturity and also afford a simple breeding opportunity to combine characteristics or traits that may be difficult to combine in other ways. Hybrid vigour in plants is generally of sufficient magnitude to warrant commercial exploitation. Commercial hybrids are used extensively in many crops including corn, sorghum, sugar beet, sunflower and canola. However, owing mainly to the lack of economical hybrid seed production methods, wheat, barley and rice are still grown mainly as inbreds.

Traditionally, hybrid seed production involves planting out separate blocks of female and male parent lines with only the seed from the female parents being harvested. To ensure that this seed is hybrid, self pollination of the female parent line must be minimised by rendering the line male-sterile. Methods for making the female parent line male sterile include mechanical, chemical and genetic methods. In monoecious plants, such as maize, male sterility can be readily achieved mechanically by detasselling of the male infloresence. However most crops are diecious and having male and female organs within the same flower makes such physical emasculation impractical. Genetic approaches have therefore sometimes been used.

Genetic male sterility traits which occur are normally controlled by nuclear genes in which the alleles associated with the sterile phenotype are generally expressed recessively with respect to the corresponding alleles associated with fertility. Where genetic male sterility occurs it is normally associated with a single recessive gene that must be homozygous in order for male sterility to be expressed. In order to make practical use of such genetic male sterility traits, breeders usually develop a phenotypically uniform female line that segregates into male-sterile and male-fertile plants. The male fertile plants, once identified, need to be rogued out which is labour intensive. There is always a problem with maintaining the parental line since male fertile plants cannot be eliminated from the population because they are essential for maintenance of the population. Rather than rely on the existence of natural male sterility alleles it is also possible to use molecular biological methods. Plants may be engineered which express, for example, anti-sense or ribozyme genes that decrease or eliminate expression of key genes necessary for the formation of viable pollen. Such transgenic lines of plants are male-sterile and are used for the production of hybrid seed by crossing using pollen from male-fertile plants. The main problem with such lines is that they can only be maintained in a heterozygous state in subsequent generations, via crosses with the isogenic fertile lines. This can be a problem in hybrid seed production where yield is critical. Although, for example by linking herbicide resistance to male sterility, it may be possible to selectively rogue out the male-fertile plants this still necessitates that the plants are planted initially at extra high densities.

The use of cytoplasmic male sterility for commercial hybrid production requires a stable male-sterile cytoplasm and a source of pollen. The cytoplasmic-genetic system of male sterility requires the existence of three types of line for hybrid production, the A line (cytoplasmic male-sterile), B line (male-fertile maintainer) and R line (male fertile with restorer genes). Three-way crosses produced with this system involve maintenance and production of four lines, an A and a B line of one inbred and male-fertile inbreds of the other two. Reliance on a single source of male-sterile cytoplasm can minimise breeding flexibility and lead to progeny with wholesale susceptibility to particular diseases.

Hybrid seed can also be produced through the use of chemicals that inhibit viable pollen formation. These chemicals, called gametocides, are used to impart transitory male-sterility. However the expense, registerability and reliability of gametocides has limited their use.

A shortcoming of traditional hybrid seed production systems is the need to plant separate rows or blocks of the male and female parent lines. Here low efficiency pollination is an especially acute problem in crop species, such as wheat, that release small amounts of pollen which does not travel far on the wind. In such crops as much as two/thirds of the hybrid-producing field needs to be dedicated to male pollen-donor plants and then hybrid seed production therefore becomes uneconomic.

In order to achieve more economic seed production in wheat and other crops it is necessary to move male and female plants closer together for more efficient pollen transfer; most efficiently by interplanting males and females within centimetres of each other in the same rows. In such a system it would be impractical to harvest only the seed from the (male-sterile) female parents. The contamination with non-hybrid seed originating from the male parent can be minimised by using as low a percentage of such male parent plants in the planting mix as possible and/or by using male plants which are female sterile. A method for constructing a dominant female sterile line has been described (EP 412,006 A1 (1990); Goldman et al., (1994) EMBO. J., 13, 2976-2984) but, as with the male sterile lines, the line has to be maintained as a heterozygote.

Accordingly there remains a need for simple economic methods of hybrid seed production. In particular, in order efficiently to produce hybrid seed there remains a need to provide both male-sterile female parental lines and female-sterile male parental lines which can be easily maintained as pure homozygous lines and which are useful for efficient hybrid seed production. Methods which are described in the art for achieving this include methods wherein hybrid seed is produced from male and female parent lines at least one of which comprises a heterologous chimeric gene, preferentially expressed in floral tissue, which renders the line conditionally sterile dependent upon the exogenous application of a non-phytotoxic substance which can be specifically and locally converted to a phytotoxin by an enzyme which is encoded by the heterologous chimeric gene and which is preferentially expressed in either the male or female reproductive structures. The non-phytotoxic substance may be a pro-herbicide. The advantage of having such conditionally sterile parent lines is that it allows them to be maintained as homozygotes with respect to the sterility trait. Fertility is only disrupted upon exogenous application of the non-phytotoxic substance. In one such example of a conditional male sterility system a gene encoding a deacetylase enzyme is preferentially expressed in tapetal cells of male flower tissue where it converts the exogenously applied pro-herbicide N-acetyl L phosphinothricin to the phytotoxin L phosphinothricin and thus prevents viable pollen formation. In further similar examples: (i) tapetum preferential expression of a bacterial cytochrome P450 catalyses conversion of pro-herbicide R7402 to a sulphonylurea phytoxin which prevents the production of viable pollen; and (ii) tapetum preferential expression of a phosphonate monoester hydrolase catalyses conversion of glyceryl glyphosate pro-herbicide to the phytotoxin glyphosate which also prevents production of viable pollen. WO 98/03838 describes examples of a conditional female sterility system wherein enzymes capable of converting the pro-herbicides to phytoxins are preferentially expressed in female reproductive structures.

Despite the existence of these methods for making male and female parent lines that are conditionally sterile, hybrid seed production remains far from routine in crops such as wheat. The current inventions concern, inter alia, improvements in the art with respect to the generation of female parent lines which are conditionally male sterile and male parent lines which are conditionally female sterile.

The current invention relates to improvements in methods for the production of crop hybrid seed. In particular the invention relates to a method of hybrid seed production from male and female parent lines at least one of which is conditionally female or male sterile dependent upon the exogenous application of a substance which is non-phytotoxic to the crop and which include pro-herbicides. The invention further relates to a method in which the said non-phytotoxic substance is applied at a time and in sufficient amount that self fertilization is minimised or prevented in the conditionally sterile parent line(s). The current invention also relates to a method of generating conditionally male or female-sterile plants by i) transforming plant material with one or more chimeric genes which, singly or together, encode one or more enzymes capable of reacting with a non-phytotoxic substance, preferably in the form of a pro-herbicide, to produce a phytotoxic one. Enzymes are expressed under operable control of one or more promoters which, in the case of conditionally male sterile plants, causes the enzyme(s) to be expressed preferentially in the male reproductive structures or which, in the case of conditionally female sterile plants, causes the said enzyme(s) to be expressed preferentially in the female reproductive structures. The plant material is regenerated into morphologically normal fertile plants which are conditionally male or female sterile. The invention also includes the use of conditionally male-sterile plants in combination with conditionally female-sterile plants to produce more efficiently hybrid seed, the use, as non-phytotoxic substances, of certain pro-herbicides and the use of chimeric genes to produce more efficiently hybrid seeds, chimeric genes and enzymes useful for the invention. The invention also provides conditionally male-sterile, conditionally female-sterile plants, seeds of these plants and hybrid seeds produced by the method. In preferred embodiments of the invention the crop plants to which the method for making hybrid seed is applied are maize, rice, sorghum, wheat, millet, oats, canola and barley.

According to the present invention there is provided a method of producing male or female sterile plants comprising the steps of transforming plant material with a polynucleotide which encodes at least one enzyme which reacts with a non-phytotoxic substance to produce a phytotoxic one, and regenerating the thus transformed material into a plant, wherein the said non-phytotoxic substance is applied to the plant up to the time of male or female gamete formation and/or maturation, so that the non-phytotoxic substance provides for the production of a phytotoxic one which selectively prevents the formation of or otherwise renders the said gametes non-functional, wherein the enzyme is expressed preferentially in either male or female reproductive structures, characterised in that (i) the non-phytotoxic substance is selected from the group consisting of ester derivatives of non-phosphonate herbicides which herbicides are directly phytotoxic to non-green tissue, D-alpha amino acids, peptide derivatives of non-protein D-alpha amino acids, S-enantiomers of aryloxyphenoxypropionates and S-enantiomers of ester derivatives of aryloxyphenoxypropionates and (ii) the enzyme is selected from the group consisting of carboxylesterases, D-amino acid oxidases, D-amino acid dehydrogenases, D-amino acid racemases, 2-arylpropionyl-CoA epimerases, alpha-methylacyl-CoA racemases, thioesterases and acyl-CoA synthetases.

Since it is a desirable objective to maximise the yield of hybrid seed and therefore to minimise any crop damage, in preferred embodiments, the non phytotoxic substance is a pro-herbicide selected from amongst compounds which are relatively non-phytotoxic to the crop. In order to be capable of an effect against floral tissues it is also desirable that pro-herbicides be progenitors of phyto-toxins that are effective in 'non-green' tissues. Thus, in preferred embodiments of the invention, pro-herbicides are selected from those which are progenitors of phyto-toxins which are directly phytotoxic to non-green tissues rather than those which have a principle site of action in photosynthesis or in the generation of photosynthetic pigments. It is also a desirable objective to minimise the costs of hybrid seed production. Thus, in preferred embodiments, pro-herbicides are selected from amongst those chemical substances for which approval from appropriate regulatory authorities for use in crops is either already granted or is pending.

NOMENCLATURE

Definitions

'Gene' as used herein refers to any DNA sequence comprising several operably linked DNA fragments such as a promoter and a 5' regulatory region, a coding sequence and an untranslated 3' region comprising a polyadenylation site.

'Chimeric' when referring to a gene or DNA sequence is used to refer to the fact that in nature, the coding sequence is not associated with the promoter or with at least one other regulatory region of the DNA in the gene.

'Chimeric gene' as used herein refers to a gene wherein, in nature, the coding sequence is not associated with the promoter or with at least one other regulatory region of the DNA in the gene.

'Expression cassette' as used herein refers to a transferable region of DNA comprising a chimeric gene which is flanked by one or more restriction or other sites which facilitate precise excision from one DNA locus and insertion into another.

'Non-phytotoxic substances' are, in the context of the current invention, substances which are relatively non-phytotoxic to plants, cells or tissues of any particular crop to which the method of the invention is applied. Non-phytotoxic substances need not be non-phytotoxic in all plant tissues of all plants. Non-phytotoxic substances include pro-herbicides which are substances with no appreciable direct toxic effect on plant tissues but which are progenitors of active phyto-toxins. In susceptible plant species such pro-herbicides act indirectly as herbicides through the action of endogenous enzymes which convert them in planta to a phyto-toxin.

'Phyto-toxins' are, in the context of the current invention, substances which are toxic to plants, plant tissues and plant cells of the particular crop to which the method of the invention is applied. Such phyto-toxins need not be phyto-toxic to all plant tissues from all plant species.

'Female reproductive structure' means the female gametes and those portions of the plant that are specialised for the production, maturation and viability of female gametes. Normally this comprises those portions of a plant that comprise the carpel or gynoecium ("pistill"). The carpel of a plant includes but is not limited to, a stigma, style, ovary and cells or tissues that are comprised by the stigma, style and ovary.

'Male reproductive structure' means the male gametes and those portions of the plant that are specialised for the production, maturation and viability of male gametes. This comprises those portions of a plant that comprise, for example, microspores, stamens, tapetum, anthers and the pollen.

'Female-sterile plant' as used herein is a plant that is incapable of supporting viable seed formation when pollinated with functional or viable pollen. Such female sterility can be the result of breeding selection or the presence of a transgene. A 'conditionally female-sterile plant' refers to a plant which under normal growing conditions is female fertile and which can become female-sterile under specific conditions. In the context of the current invention the said conditions comprise the exogenous application of a pro-herbicide or other non-phytotoxic substance. In the context of the current invention such a 'female-sterile plant' or 'conditionally female-sterile plant' remains male fertile and able to produce viable pollen.

'Male-sterile plant' as used herein is a plant that is incapable of supporting viable pollen formation. Such male sterility can be the result of breeding selection or the presence of a transgene. A 'conditionally male-sterile plant' refers to a plant which under normal growing conditions is male fertile and which can become male-sterile under specific conditions. For example the conditions might comprise physical emasculation or application of a specific chemical gametocide. In the context of the current invention the said conditions particularly comprise the exogenous application of a pro-herbicide or other non-phytotoxic substance. In the context of the current invention such a 'male-sterile plant' or 'conditionally male-sterile plant' remains female fertile and able to produce viable seeds when pollinated with functional or viable pollen.

'Promoter region' as used herein is a region of DNA comprising at least a functional promoter and, optionally, some or all of its associated upstream regulatory sequences including enhancer sequences and/or associated downstream sequences including some or all of the 5' untranslated region of the gene endogenous to the promoter.

'Inter-planting' as used herein refers to a method of planting seeds or plants in a field that ensures adequate cross-pollination of male sterile or conditionally male-sterile plants by the male-fertile plants. This can be achieved either by random mixing of female and male parent seed in different blends (80/20; 90; 10; etc) before planting or by planting in specific field patterns whereby different seeds are alternated. When separate harvesting from different plants is required planting in alternating blocks or rows is preferred.

'Carboxylesterase' as used herein only encompasses enzymes that are properly classified as EC 3.1.n.

In the method according to the invention the said non-phytotoxic substance may be applied in mixture along with at least one further substance which may be selected from the group consisting of amino acids, safeners, gametocides, glutathione-S-transferase inducers, cytochrome P450 inducers, fertilizers, herbicides, nematocides, synergists, insecticides, fungicides, hormones, plant-growth regulators and cytochrome P450 inhibitors. In particular embodiments the said non phytotoxic substance may be applied in mixture with piperonyl butoxide or malathion. In particular embodiments the said non-phytotoxic substance may be applied in a mixture with the same phytotoxic substance that the non-phytotoxic substance is a progenitor of.

The enzyme used in the method of the invention may be a carboxylesterase and the non-phytotoxic substance may be an ester of imazamethabenz or of flamprop. In a particularly preferred form of the invention which relates specifically to wheat, the non-phyto-toxic substance is a pro-herbicide selected from the group consisting of imazamethabenz methyl, flamprop methyl or flamprop isopropyl.

The said enzyme may be a D-amino acid oxidase, a D-amino acid dehydrogenase or a D-amino acid racemase and the non-phytotoxic substance may then be a D amino acid and, in particular, it may be the D enantiomer of phosphinothricin, the D enantiomer of bialaphos or selected from the group consisting of D-alanine, D serine, D isoleucine, D methionine, D leucine or D valine. As used herein "D amino acid oxidase" means any enzyme capale of oxidising a D-amino acid to produce a 2 keto acid and includes enzymes with specificity for aspartate known as "D-aspartate oxidases".

Alternatively, the enzyme used in the present inventive method may be selected from the group consisting of 2-arylpropionyl-CoA epimerases, alpha-methylacyl-CoA racemases, thioesterases and acyl-CoA synthetases and the non-phytotoxic substance may then be an S enantiomer of an aryloxyphenoxypropionate or an S enantiomer of an aryloxyphenoxypropionate ester.

Chimeric genes encoding enzymes capable, singly or in combination with others, of reacting with a non-phytotoxic substance to produce a phytotoxic one may be selected from amongst genes comprising DNA coding sequences which encode one or more of the following enzymes.

(1) Carboxylesterases capable of catalysing the hydrolysis reaction:

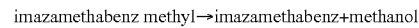
imazamethabenz methyl→imazamethabenz+methanol (2) Carboxylesterases capable of catalysing the hydrolysis reaction:

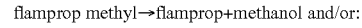
flamprop methyl→flamprop+methanol and/or:

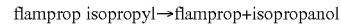
flamprop isopropyl→flamprop+isopropanol (3) D-amino acid oxidases capable of catalysing the oxidation:

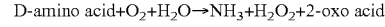
D-amino acid+$O_2$+$H_2O$→$NH_3$+$H_2O_2$+2-oxo acid and in certain embodiments particularly the reaction

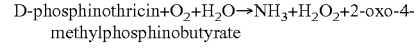
D-phosphinothricin+$O_2$+$H_2O$→$NH_3$+$H_2O_2$+2-oxo-4-methylphosphinobutyrate (4) D-amino acid dehydrogenases capable of catalysing the oxidation:
D-phosphinothricin+electron acceptor+$H_2O$→$NH_3$+ 2e− reduced electron acceptor+2-oxo-4-methylphosphinobutyrate. The D-amino acid dehydrogenases may be membrane-associated enzymes which couple electrons via an electron acceptor to a membrane-bound electron transport chain from which the ultimate electron recipient may, for example, be $NAD^+$ or $O_2$ (5) Amino acid racemases capable of catalysing the interconversion:

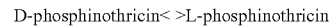
D-phosphinothricin< >L-phosphinothricin (6) 2-arylpropionyl-CoA epimerases or alpha-methylacyl-CoA racemases capable of catalysing one or more of the following reactions:

S-Fluazifop-CoA→R-Fluazifop-CoA and/or

S-Quizalofop-CoA→R-Quizalofop-CoA and/or

S-Propaquizafop-CoA→R-Propaquizafop-CoA and/or

S-Haloxyfop-CoA→R-Haloxyfop-CoA and/or

S-Fenoxaprop-CoA→R-Fenoxaprop-CoA and/or

S-Diclofop-CoA→R-Diclofop-CoA and/or

S-Cyhalofop-CoA→R-Cyhalofop-CoA and/or

S-Clodinafop-CoA→R-Clodinafop-CoA (7) Thioesterases capable of catalysing the hydrolysis reaction:

R-Fluazifop-CoA→R-Fluazifop+CoA and/or

R-Quizalofop-CoA→R-Quizalofop+CoA and/or

R-Propaquizafop-CoA→R-Propaquizafop+CoA and/or

R-Haloxyfop-CoA→R-Haloxyfop+CoA and/or

R-Fenoxaprop-CoA→R-Fenoxaprop+CoA and/or

R-Diclofop-CoA→R-Diclofop+CoA and/or

R-Cyhalofop-CoA→R-Cyhalofop+CoA and/or

R-Clodinafop-CoA→R-Clodinafop+CoA (8) Acyl-CoA synthetases capable of catalysing the reaction:

S-Fluazifop+CoA+ATP→S-Fluazifop-CoA+PPi+AMP and/or

S-Quizalofop+CoA+ATP→S-Quizalofop-CoA+PPi+AMP and/or

S-Propaquizafop+CoA+ATP→S-Propaquizafop-CoA+PPi+AMP and/or

S-Haloxyfop+CoA+ATP→S-Haloxyfop-CoA+PPi+AMP and/or

S-Fenoxaprop+CoA+ATP→S-Fenoxaprop-CoA+PPi+AMP and/or

S-Diclofop+CoA+ATP→S-Diclofop-CoA+PPi+AMP and/or

S-Cyhalofop+CoA+ATP→S-Cyhalofop-CoA+PPi+AMP and/or

S-Clodinafop+CoA+ATP→S-Clodinafop-CoA+PPi+AMP

The carboxylesterase enzyme may be selected from carboxylesterase B (EC 3.1.1.1) type enzymes, especially those that are derived from *Arthrobacter* sp, *Bacillus* sp, pig liver, *Saccharomyces* sp or *Synechocystis* sp. Preferred such enzymes may be selected from amongst proteins having the Swissprot accession numbers Q01470, P37967, Q29550 (the mature peptide sequence from 60-1703), P40363 or SEQ ID number 2 (this application), and the DNA sequence encoding the carboxylesterase enzyme may be selected from amongst DNA sequences comprised within EMBL accessions M94965, BS06089, SSCE, Z34288 and SEQ ID number 1 (this application). Further carboxylesterase enzymes and DNA coding sequences suitable for working the invention are selected from amongst plants and microorganisms which, in a minimal medium, are found to exhibit similar sensitivity to growth inhibition by imazamethabenz methyl as by imazamethabenz. Candidate esterase genes from DNA libraries of such organisms are identified using suitable DNA probes and isolated by subcloning. Alternatively, genes encoding suitable enzymes are identified and selected from expression libraries in suitable imazamethabenz methyl insensitive host organisms via screening for transformation to the imazamethabenz methyl sensitive phenotype. Equally, suitable and improved genes and enzymes are selected on the basis of expression in *E. coli* and, either in vivo or in vitro, assay for the desired flamprop ester or imazamethabenz ester esterase activity via the usual methods including detection of imazapyr or flamprop by inhibition of target enzymes such as acetohydroxyacid synthase, by HPLC/LW and/or by derivitization and GC MS.

The D-amino acid oxidase (DAMOX) enzyme may be selected from amongst those produced by *Rhodosporidium* sp. (*Rhodotorula* sp.), *Trigonopsis* sp, pig, *Fusarium* sp, *Candida* sp, *Schizosasaccharomyces* sp and *Verticillium* sp, and may selected from proteins having sequences corresponding to Swissprot accession numbers P80324, Q99042, P00371, P24552 or SPTREMBL numbers Q9HGY3 and Q9Y7N4. The DNA sequences which encode the D amino acid oxidase may be selected from sequences comprised within EMBL accessions A56901, RGU60066, Z50019, SSDA04, D00809, AB042032, RCDAAOX, A81420 and SPCC1450. D-amino acid oxidases are ubiquitous flavoenzymes.

Where the non-phytotoxic substance is D phosphinothricin or D-bialaphos or D-aspartate or D-ghitamate then particularly preferred D-amino acid oxidases are obtained from *Rhodotorula gracilis* mutants or is a D-aspartate oxidase. Such mutants, whatever the non-phytotoxic substance, may comprise single and double amino acid substitutions at positions 213 and 238 when compared with the wild type sequence. Preferably at position 213 the wild type methionine is replaced by Arg, Lys, Ser, Cys, Asn or Ala, and the wild type Tyr at position 238 is replaced by His, Ser, Gys, Asn or Ala.

However, the enzyme may comprise substitutions in addition to, or at other than, the positions mentioned in the preceding paragraph. In particular, the Phe at position 58 in the wild type sequence may be replaced by a residue selected from the group consisting of His, Ser, Lys, Ala, Arg, and Asp, and preferably is either His, Ser or Ala. In addition, or alternatively, the Met at position 213 in the wild type sequence may be replaced by a residue selected from the group consisting of His, Ser, Lys, Ala, Arg, and Asp, and preferably is either Ser or Ala. In addition, or alternatively, the Tyr at position 223 in the wild type sequence may be replaced by a residue selected from the group consisting of His, Ser, Ala, Arg, and Asp. In addition, or alternatively, the Tyr at position 238 in the wild type sequence may be replaced by a residue selected from the group consisting of His, Ser Lys, Ala, Arg, and Asp.

A particularly preferred mutant form of the enzyme comprises at least two of the above mentioned mutations. A first embodiment of such a double mutant has His at position 58 (rather than Phe in the wild type sequence), and Ser at position 213 (rather than Met). A second embodiment of such a double mutant has Ser at position 58 (rather than the wild-type Phe) and Arg at position 213 (rather than the wild-type Met).

Where the non-phytotoxic substance is a D-amino acid other than D phosinothricin or D-bialaphos then the enzyme is a D-amino acid oxidase. The D amino acid is preferably, not an endogenous plant metabolite and is selected to be one that is phloem mobile, metabolically stable in the plant (preferably having at t ½ in the plant of greater than ~1 week) and an efficient substrate of the said oxidase. Oxidation of the D-amino acid by the enzyme is concomitant with reduction of oxygen to phytotoxic peroxide and/or superoxide anions.

In a preferred embodiment the oxidase enzyme is targeted to a subcellular location other than the peroxisome. This is achieved, for example, by modifying the gene so that three C-terminal amino acids (e.g. SKL in the case of the *Rhodotorula gracilis* D amino acid oxidase) are deleted or modified and/or by addition of sequence to add a chloroplast or mitochondrial transit peptide to the N-terminus.

Further suitable D amino acid oxidases may be obtained preferably from fungal sources, by the mutation and selective procedures known to the skilled man and augmented by the present disclosure.

Further D amino acid oxidase (or equally, phosphinothricin racemase) enzymes and DNA coding sequences suitable for working the invention are selected from amongst those organisms, optionally subjected to mutagenesis, where it is found that growth on a N-limited media, under conditions where D-amino acid oxidase (or phosphinothricin racemase) is induced (for example grown on D-alanine) is selectively inhibited in the presence of D-phosphinothricin. D-amino acid oxidase genes suitable for the invention are then, for example, obtained by probing gene libraries of such organisms with suitable degenerate DNA probes (for example based upon established D-amino acid oxidase concensus sequences such as PROSITE, PS00677) and subcloning. Alternatively, genes encoding suitable enzymes are obtained by screening gene expression libraries in a suitable host cell such as *E. coli* or a yeast (suitable host strains lack an endogenous oxidase or dehydrogenase activity versus D-phosphinothricin) for transformation to a phenotype with increased sensitivity to growth inhibition by D-phosphinothricin on a minimal medium. This method relies upon the ability of transformed *E. coli* clones to produce L-PPT from D-PPT via the combined action of their endogenous L transaminase activity and the heterologous oxidase. Alternatively, suitable and improved genes are selected on the basis of in vitro assay of the expressed enzyme for the desired ability to oxidise D-phosphinothricin. There are many methods for directly assaying the activities of D-amino acid oxidases such as based upon detection of peroxide (Enzyme Microb. Technol., (2000), 27(8), 605-611), depletion of oxygen using an oxygen electrode or based on direct detection of ammonia.

In an embodiment of the invention, a preferably fungally-derived DAMOX gene is cloned into a shuttle vector under operable control of a promoter (e.g GAL promoter) capable of expression in the host organism in which the selection will be carried out (preferably yeast) This gene is then subjected to mutagenesis, for example by Mn2+-poisoned PCR; plasmid DNA replication in a strain which is defective in DNA repair/editing processes such as *E. coli* strain XL1 red; or by plasmid DNA replication in a host strain which is subjected to mutagenesis using, for example X-Rays, UV light, addition of a chemical mutagen and transformed into a host organism (preferably yeast). The desired DNA encoding a DAMOX having the desired property of an enhanced ability to oxidise D-PPT is selected for (following an optional, initial selection step for transformants based upon selectable markers present on the shuttle vector allowing, for example, selection via restoration of prototrophy or growth in presence of hygromycin etc) via, for example.

a) Selection of transformed cells having the ability to utilise amino acids which are chemically similar to D-phosphinothricin as sole nitrogen source. For example, transformed yeast colonies are selected which are able to grow on analogues of D-PPT (and its esters) where the phosphinic acid moiety is replaced with a carboxylate (i.e D-glutamate), sulphonate, phosphonate, sulphone, or sulfoxide moiety (or esters of these) as sole N source. E.g.

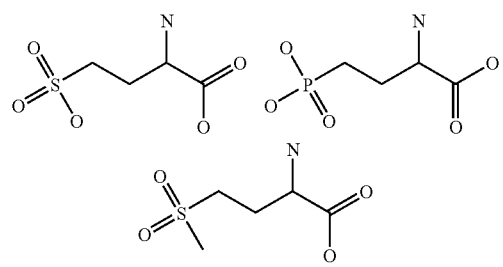

b) Selection of transformed cells capable of utilizing D-PPT itself as sole N source. For this selection to work, the host cell must also be transformed with a gene capable of negating the inhibitory effect of L-phosphinothricin on glutamine synthetase. For example the shuttle vector may also comprise a gene which encodes an enzyme such as PAT which inactivates L-PPT.

Cycles of mutation and selection may be iterated. D-amino acid oxidases may further be cloned, expressed, part purified and characterised kinetically in order to identify genes and DAMOXs with the most suitable properties (e.g enzyme stability, high kcat/Km value for oxidation of D-PPT, minimal oxidation of any endogenous plant substrates, optimum pH optimum etc).

Where the non-phytotoxic substance is D-phosphinothricin (PPT) it may be obtained from a mixture of D and L PPT. For example, DL PPT may be added to a culture medium (preferably minimal) of *E. coli* cells (optionally an arg E mutant to minimise the background level of N-acetyl PPT deacetylase activity) transformed and induced to express a PAT gene (encoding an enzyme which transfers an acetyl group from acetyl CoA to L-PPT) at a high level. After allowing a suitable time for the L component to substantially all be N-acetylated, (judged, for example, by monitoring the conversion using 31-P NMR) D-PPT is recovered and purified from the cell-free medium using successive steps of, for example, solvent extraction at high and low pH, anion and cation exchange chromatography, selective crystallisation with chiral cations such as chinchocine or other procedures known in the art such as liquid/liquid extraction with two non-miscible aqueous phases as the phase system (cf methods in U.S. Pat. No. 5,153,355). Typically a late step is cation exchange chromatography from which D-PPT is recovered as the ammonium salt Alternatively, D-PPT may be obtained by an enzymatic method wherein DL PPT+2 ketoglutarate is converted to primarily a mixture of D PPT, 2-oxo PPT (and its decarboxylation products) and GABA by the combined actions of (I) L-aminotransferase (e.g from *E. coli*) and (II) glutamate decarboxylase. The desired pure D PPT is resolved from the reaction mixture using methods known in the art and as outlined above.

D PPT may also be obtained using an enzymatic method wherein DL PPT+2 ketoglutarate+NAD is converted to primarily a mixture of D PPT, 2-oxo PPT (and its decarboxylation products) NADH, and ammonia by the combined actions of (I) L-aminotransferase and (II) glutamate dehydrogenase. The desired D PPT is purified from the reaction mixture.

In a yet further method of making D-PPT, DL PPT is treated with a L amino acid oxidase so that the only remaining amino acid is the desired D form. This D-PPT is then purified from the reaction mixture.

A still further method involves (I) conversion of DL PPT to N-acetyl DL PPT (using acetic anhydride or other acetylating reagents and methods well known in the art) and (II) treatment of N-acetyl DL PPT with D-aminoacylase so that only N acetylD-PPT is deacetylated. The resultant D-PPT is purified from the reaction mixture. For example, D-PPT is resolved from N-acetyl-L-PPT by binding to Dowex anion exchange resin and elution with 40 mM formic acid. Under suitable loading conditions this acid elutes the D-PPT whilst leaving the N-acetyl L-PPT bound to the column.

A still further method involves treatment of DL PPT with L-aminoacylase and an acylating agent in a non-aqueous solvent so that only the desired D-PPT is left in a non-acetylated form.

A yet further method of preparing pure D-PPT involves enantioselective crystallisation from DL PPT using a chiral base such as chinchocine and addition of a seed crystal of the chiral base with pure D-PPT.

A yet further method of preparing pure D-PPT from DL-PPT by direct chiral chromatography using a chiral base column.

A detailed method for the production of pure D-PPT is given in one of the Examples following.

The 2-arylpropionyl-CoA epimerase or alpha-methylacyl-CoA racemase (EC 5.1.99.4) enzyme may be selected from amongst those produced by rat liver, *Acremomium* sp or *Neurospora crassa*. The 2-arylpropionyl-CoA epimerase or alpha-methylacyl-CoA racemase (EC 5.1.99.4) enzyme may be selected from proteins having sequences corresponding to AAR49827 in the GENESEQP Derwent database, P70473 in Swissprot or SEQ ID number 4 (this application) and the 2-arylpropionyl-CoA epimerase or alpha-methylacyl-CoA racemase (EC 5.1.99.4) enzyme may be encoded by a DNA coding sequence selected from sequences comprised within GENESEQN Derwent database accession AAQ44447, EMBL accessions RN2ARYLCO and RNU89905 and SEQ ID number 3 (this application).

The acyl CoA synthetases for use in the invention may be 'long-chain' acyl CoA synthetases (EC 6.2.1.3) selected from those produced by *Brassica napus*, rat liver, *Saccharomyces* sp or *Arabidopsis*. The said synthetases may be selected from proteins having sequences corresponding to SPTREMBL sequence Q96338, Swissprot P18163, Swissprot P39518, SPTREMBL Q9C5U7 or SPTREMBL Q9TOAO and the DNA sequences which encodes the acyl CoA synthetases may be selected from sequences comprised within EMBL accessions BNAMPBP2, J05439, X77783 and AB030317.

The acyl CoA synthetases, 2-arylpropionyl-CoA epimerases and thioesterase enzymes and/or DNA sequences which encode them which are suitable for working the method of the invention may be selected on the basis of the capability of the source organism to convert S-aryloxyphenoxypropionates to R-aryloxyphenoxypropionates and/or to convert S-ibuprofen to R-ibuprofen. Such organisms can, for example, be obtained from soil samples and methods for assaying and detecting such chiral inversions in cell cultures and microbial broths are well-known (cf Menzel-Soglowek et al. (1990) J. Chromatogr., 532, 295-303; Bewick (1986) Pestic. Sci., 17, 349-356). Accordingly, the acyl CoA synthetase, 2-arylpropionyl-CoA epimerase and/or thioesterase enzyme and, optionally, the DNA sequences which encode them may be sourced from, *Arthrobacter* simplex NCIB 8929; *Arthrobacter roseoparaffineus* ATCC 15584; *Bacillus subtilis* ATCC 15841; *Botrytis cinerea* CM1 124882; *Brevibacterium butanicum* ATCC 15841; *Brevibacterium healii* ATCC 15527; *Brevibacterium ketoglutamicum* ATCC 21004; *Brevibacterium paraffinolyticum* ATCC 21195; *Corynebacterium fascians*; *Corynebacterium fijikoense* ATCC 21496; *Methanomonas methanolica* NRRL B-5758; *Micrococcus roseus*; *Mycobacterium aurum* NCTC 1043; *Mycobacterium petroteophilum* ATCC 21497; *Mycobacterium phlei* NCTC 10266; *Mycobacterium smegmatis* ATCC 19420; *Nocardia opaca* NCIB 9409; *Nocardiopsis asteroids* ATCC 21943; *Psuedomonas dimimuta* NCIB 9393; *Psuedomonas lemoignei* NCIB 9947; *Rhodococcus rhodocrous* ATCC 13808; *Rhodococcus rhodocrous* ATCC 21197; *Rhodococcus* sp ATCC 21499; and *Rhodococcus* sp ATCC 31337. Using methods well known in the art, candidate and improved genes comprising DNA coding sequences are readily cloned and selected from suitable gene libraries of these organisms by the use of suitably degenerate probes based upon the known sequences of other acyl CoA synthetase, 2-arylpropionyl-CoA epimerase and thioesterase enzymes. Alternatively and additionally suitable genes are selected on the basis of preparing expression libraries in a suitable host and screening the library, using either in vitro or whole organism culture assays, for ability of clones to carry out the overall chiral conversion or, alternatively, for ability to catalyse each of the individual acyl CoA synthetase (using the microsomal fraction), 2-arylpropionyl-CoA epimerase or thioesterase partial reactions. Suitable methods for in vitro assays of these activities are analogous to or the same as those described in the literature for ibuprofen (e.g. Shieh and Chen (1993) JBC, 268, 3487-3493.

The enzyme for use in the present inventive method may be a phosphinothricin racemase, the DNA coding sequence for which is produced by mutagenesis and/or recombinatorial shuffling of glutamate racemase genes followed by iterative rounds of selection and further evolution toward increasing levels of phosphinothricin racemase activity. Glutamate racemases are ubiquitous amongst bacteria and are of two types, those that are dependent on pyridoxal phosphate as a cofactor and those which are cofactor-independent and contain two active-site cysteine residues. In one embodiment of the invention, sequences encoding glutamate racemases of *Pediococcus pentosaceus*, *Lactococcus lactis*, *Lactobacillus brevis*, *Staphylococcus hemolyticus* and *Bacillus sphaericus* are selected for mutation and/or recombinatorial family shuffling. In a particular embodiment the genes selected for shuffling encode proteins having sequences corresponding to (Swissprot) sequences O82826, P94556 and O31332. Genes suitable for working the current invention are selected by screening expression libraries in a suitable host cell such as *E. coli* or yeast those colonies which exhibit increased sensitivity to growth inhibition by D-phosphinothricin in minimal medium. L-PPT inhibits glutamine synthetase while D-PPT does not. A glutamate racemase mutant clone which converted D- to L-PPT will not grow on minimal medium unless supplemented with glutamine. In suitable host strains, endogenous D-amino acid oxidase or D-amino acid dehydrogenase activities are either not expressed or do not encompass D-phosphinothricin as a substrate. Alternatively suitable genes may be selected on the basis of assay, in vitro or in vivo, of the ability of the encoded enzyme to interconvert D and L phosphinothricin. Suitable such assays may be based upon exchange of the alpha proton, the use of bioassays to detect L-phosphinothricin formation from D-phosphinothricin or, for example, detection of conversion of L-phosphinothricin to D-phosphinothricin using coupling to a suitable D-amino acid oxidase.

DNA sequences encoding the enzymes used in the present invention may, optionally, be further mutated and selected in order to generate further useful enzymes having improved utility. Many characteristics of enzymes are thus improved including catalytic activity (kcat/Km) versus the desired substrate, temperature stability and pH optimum. Methods for generating, screening and selecting for such improved variants are well known. For example, suitable variant DNA sequences are generated by a process of mutagenesis (e.g by passaging DNA through bacterial or yeast strains with error-prone DNA replication such as *E. coli* XL1 red, by UV, chemical or targeted oligonucleotide PCR mutagenesis). In particular such genes are produced by any of a number of alternative processes of DNA shuffling or 'sexual PCR' as, for example, summarised in WO 0061740 from pages 28-41 all of which are included by reference herein. Many methods are suitable for selecting such improved genes. Genes may be suitably expressed in a suitable host cell such as *E. coli* or yeast and selected for improvement using suitable such assays as, for example, described herein.

The chimeric genes encoding enzymes for use in the invention which are capable, singly or in combination with others, of converting a non-phytotoxic substance to a phytotoxic one, may each comprise a DNA sequence which encodes one of said enzymes operably linked to a 5' promoter region which preferentially directs expression to either the male or the female reproductive structures. This specificity of expression ensures that the effect of the expressed enzyme(s) will be exerted only within the locality of the tissues and cells necessary for formation of viable seed or viable pollen and will not be deleterious to the plant beyond its effect on fertility in the presence of a suitable non phytotoxic substance, perhaps a pro-herbicide. In addition to promoter regions chimeric genes according to the current invention also comprise a 3' transcriptional terminator sequence. This is responsible for the termination of transcription and correct mRNA polyadenylation. Many such 3' transcriptional terminator sequences are known in the art and are suitable for use in the chimeric genes of the current invention. In particular embodiments the 3' transcriptional terminator sequence is selected from the CMV 35S terminator, the tml terminator, the nopaline synthase (nos) terminator and the pea rbcS E0 terminator.

5' Promoter regions suitable for use in certain embodiments of the said chimeric genes include 5' regions of genes which are preferentially expressed in female floral tissues. In certain embodiments the 5' promoter region is selected from the group consisting of the stig 1 promoter of tobacco (Goldman et al., (1994) EMBO J., 13, 2976-2984), a modified S13 promoter (Dzelkalns et al (1993) Plant Cell, 5, 8555), the AGL5 promoter (Savidge et al (1995) Plant Cell, 7, 721-733 and the promoter region 5' of the maize-carpel specific ZAG2 gene (Thiessen et al (1995) Gene, 156, 155-166). Optionally, further suitable promoter regions are obtained from regions upstream of the coding sequences of genomic DNA corresponding to cDNA sequences known in the art to be preferentially expressed in female reproductive structures. In certain embodiments such probe cDNAs are selected from the group consisting of the *Arabidopsis* Fbp7 and Fbp11 genes (Angenent et al., (1995) Plant Cell, 7, 1569-1582) and the orchid-specific cDNAs O40, O108, O39, O126 and O141 (Nadeau et al., (1996) Plant Cell, 8, 213-239). In particular embodiments 5' promoter regions comprising genomic DNA associated with preferential expression in female reproductive structures is selected from DNA regions comprised within the group consisting of the genomic DNA clone pSH64 having the accession number NRRL B-21920, genomic clone, pCIB10302 hybridising to the cDNA P26-A4 having the accession number NRRL B-21655 and genomic DNA clone X2-1 hybridising to cDNA clone P19-QA having the accession number NRRL B-21919. In further particular embodiments these promoter regions comprise nucleotides 1 to 1390 of SEQ ID No. 11, SEQ ID No. 2 and nucleotides 1 to 1093 of SEQ ID No. 4 in WO 98/39462. In further embodiments, further 5' promoter regions suitable for use in the chimeric genes of the invention are isolated and cloned by methods which are familiar to one skilled in the art. For example, novel transcripts expressed in female reproductive structures are identified by isolating RNA from tissues such as maize silks or wheat pistils followed by differential screening using techniques such as differential display, PCR select cDNA subtraction and subtractive cDNA library construction. cDNA clones that are preferentially expressed in the female tissues and not in other parts of the plant such as the leaves, roots and tassels. The tissue specificity of expression is, optionally, further confirmed by Northern blotting. The cDNA clones are used as probes for genomic library screening. 5' promoter regions and, optionally, 3' untranslated DNA regions associated with tissue preferential expression are obtained from the genomic DNA clones and used in the construction of chimeric genes for preferential expression in female reproductive structures.

5' Promoter regions suitable for use in certain embodiments of the said chimeric genes include 5' regions of genes which are preferentially expressed in male floral tissues. These include promoter regions for expression in pollen, the tapetum or other structures in the anther. In certain embodiments these 5' promoter regions are selected from the group consisting of the LAT52 promoter (Twell et al., (1989) Dev., 109, 705-713), the tomato A127 promoter (Dotson et al., (1996) Plant J., 10, 383=392), the maize Zmg promoter (Hamilton et. al., (1989) Sex. Plant Reprod. 2, 208-212), the maize CDPK promoter (Guerro et al., (1990) Mol. Gen. Genet., 224, 161-168) and the anther specific ant32 and ant43D promoters disclosed in U.S. Pat. No. 5,477,002 herein incorporated by reference in its entirety. In certain further embodiments the 5' promoter region is selected from the group consisting of the tapetum-specific promoter CA55 from maize ("Pca55" described in WO 92/13956), the tapetum-specific promoter E1 from rice (described in U.S. Pat. No. 5,639,948), the tapetum-specific promoter T72 from rice (described in U.S. Pat. No. 5,639,948), the RA8 anther-specific promoter from rice (EMBL/Genbank accession number AF042275; Jean Js et al, (1999) PMB, 39, 35-44) the anther-specific Tap1 promoter (Spena et al (1992) Theor Appl Genet. 84, 520-527) and the ZmC5-pollen specific promoter from maize (EMBL/Genbank accession number Y13285; Wakeley et al, (1998) PMB, 37, 187-192). Optionally, further suitable promoter regions are obtained from regions upstream of the coding sequences of genomic DNA corresponding to cDNA sequences known in the art to be preferentially expressed in male reproductive structures. In certain embodiments such probe cDNAs are selected from the group consisting of the orchid pollen-tube specific cytochrome P450 gene (Nadeau et al., (1996) Plant Cell, 8, 213-239), the Bcp1 gene of *Arabidopsis* (Xu et al (1995) P.N.A.S., 92, 2106-2110) and the male-flower specific MFS14 gene of maize (Wright SY et al., (1993) Plant J 3, 41-49). In further embodiments, further 5' promoter regions suitable for use in the chimeric genes of the invention are isolated and cloned by methods which are familiar to one skilled in the art. For example, novel transcripts expressed in male reproductive structures are identified by isolating RNA from tissues such as tassels, pollen tubes, anther or tapetum followed by differential screening by techniques such as differential display, PCR select cDNA subtraction and subtractive cDNA library construction. cDNA clones that are preferentially expressed in the male tissues and not in other parts of the plant such as the leaves, roots and stigma are isolated. The tissue specificity of expression is, optionally, confirmed by Northern blotting. The cDNA clones are used as probes for genomic library screening. 5' promoter regions and 3' untranslated DNA regions associated with tissue preferential expression are obtained from the genomic DNA clones and used in the construction of chimeric genes for preferential expression in male reproductive structures.

Further promoter regions useful in the chimeric genes of the invention include the regions upstream of the Osmads 13 gene of rice, the OSG gene of rice anther, and the YY2 gene of rice. Generally, promoter regions yielding high, early, sustained and preferential expression in male or female reproductive structures are selected as most suitable. Promoter regions may also further comprise chimeric combinations with each other and with further enhancer regions.

Chimeric genes may optionally comprise a region, immediately preceding the DNA sequence encoding the enzyme involved in the conversion of non-phytotoxic substance to phytotoxin, which encodes a peptide sequence capable of targeting the said enzyme to subcellular organelles such as the chloroplast, peroxisome (other than when the phytotoxin is a peroxide or super oxide anion) or mitochondria and the said targeting protein may have the sequence of (i) a chloroplast transit peptide or (ii) a chloroplast transit peptide-N-terminal portion of a chloroplast protein-chloroplast transit peptide. This may be particularly advantageous where, for example, the said DNA sequence encodes a D-amino acid dehydrogenase enzyme which would be expected to function best in a compartment such as the mitochondrion or chloroplast comprising a membrane electron transport chain or where, for example, the DNA sequence encodes an enzyme catalysing only a partial step in the overall desired transformation and where the full reaction requires combination with compartmentalised metabolites and endogenous activities. In particular, for targeting to the mitochondrion, the said region of DNA which immediately precedes the enzyme-coding DNA sequence, encodes a mitochondrial transit peptide sequence. In certain embodiments the transit peptide sequence may be selected from the group consisting of the endogenous transit peptide sequences of the beta-subunit of *Nicotinia plumbaginifolia* mitochondrial ATP synthase, mitochondria-specific NADP-dependent isocitrate dehydrogenase, NADPH-binding subunit of respiratory chain complex I and yeast mitochondrial tryptophanyl-tRNA-synthetase (WO 6121513).

Polynucleotides for use in the present inventive method may comprise one or more chimeric genes which encode enzymes which catalyse reactions involved in the generation of phytotoxins from non-phytotoxic substances. Optionally such polynucleotides comprise yet further genes and chimeric genes, such as a chimeric marker gene. A chimeric marker gene as used herein comprises a marker DNA under expression control of a promoter which is active in plant cells. The marker DNA encodes an RNA, protein or polypeptide which, when expressed in a plant, plant tissue or plant cell allows such plant material to be distinguished from plant material not expressing the marker DNA. Examples of marker genes are genes that provide a specific colour to a cell such as the A1 gene (Meyer et al. (1987) Nature 330, 667) or genes that render plant cells resistant to otherwise lethal selection with antibiotics (e.g. the aac(6') gene encoding resistance to gentamycin, WO 94/01560 or hygromycin phosphotransferase genes providing resistance to hygromycin) or herbicides such as glyphosate (e.g EPSPS genes such as in U.S. Pat. No. 5,510,471 or WO 00/66748), phenmedipham (e.g. pmph gene U.S. Pat. No. 5,347,047; U.S. Pat. No. 5,543,306), bromoxynyl (e.g. genes described in U.S. Pat. No. 4,810,648) sulphonylureas (e.g. genes described in EP 0360750), dalapon (genes described in WO 99/48023), cyanamide (genes described in WO 98/48023; WO 98/56238) and genes encoding resistance to glutamine synthetase inhibitors such as L-phosphinothricin (such as, for example, N-acetyl-transferase genes described in EP 0242246, EP 0242246 and EP 0257542). In a preferred embodiment of the polynucleotide of the current invention which comprises a herbicide resistance gene as a marker gene, the said herbicide is a herbicide which is useful for weed control in the crop and, additionally, the herbicide resistance gene is expressed sufficiently to provide robust tolerance to field rates of the said herbicide. In a further preferred embodiment the herbicide is glyphosate and the herbicide resistance gene is an EPSP synthase. However the marker gene may be a gene that provides for positive selection wherein the marker gene encodes an enzyme which provides, in the context of a particular medium, the transformed plant cells with a positive metabolic advantage. U.S. Pat. No. 5,767,378 describes a number of suitable positive selection systems and genes.

Where the polynucleotide of the current invention comprises a herbicide resistance gene the herbicide is exogenously applied to crop plants which are interplanted at a sufficient density to eliminate the production of non-hybrid seed originating from non-transgenic self-fertile parent plants. In a preferred embodiment the herbicide is glyphosate or an agronomically useful salt thereof and the said herbicide resistance marker gene is selected from amongst those glyphosate resistance conferring genes described in WO 00/66748.

Where a marker gene is present, means for the removal of said marker gene may also be provided. This is desirable where, for example, it is decided to combine traits. In addition it is also desirable to remove herbicide-resistance marker genes which could interfere with the operation of the pro-herbicide-dependent conditional fertility mechanism of the present invention. For example, it might be desirable to remove a phosphinothricin N acetyl transferase (PAT) herbicide-resistance marker gene from a polynucleotide also comprising a chimeric gene, useful for providing conditional male or female sterility dependent on the exogenous application of D-phosphinothricin pro-herbicide. The presence of the PAT gene could potentially interfere with successful conditional sterility by inactivating the L phosphinothricin phytotoxin. Thus, polynucleotides which comprise marker genes may optionally comprise specific recognition sites for specific recombinases in positions which flank the marker gene and which allow the sequence to be 'kicked out'. Crossing of a plant carrying the so-flanked marker gene with a plant carrying a gene which encodes the corresponding specific recombinase results in progeny plants from which the marker is specifically excised. Examples of suitable such site-specific homologous recombination systems are the flp/frt system (Lyznik et al., (1996), Nucleic Acids Res. 24, 3784-3789) and the Cre/Lox system (Bayley, C. C. et al., (1992) PMB, 18, 353-361).

Polynucleotides used in the present inventive method may optionally comprise one or more translational enhancers located within the non translated regions 5' of the protein-encoding sequences. The skilled man is aware of the identity of such suitable translational enhancers—such as the Omega and Omega prime sequences derived from TMV and that derived from the tobacco etch virus, and how such translational enhancers can be introduced into the polynucleotide so as to provide for the desired result of increased protein expression. Further examples include translational enhancers derived from maize chlorotic mottle virus and alfalfa mosaic virus (Gallie et al., (1987) Nucl. Acids Res., 15, 8693-8711; Skuzeski et al., (1990) PMB., 15, 65-79). To further optimise expression of proteins from chimeric genes and chimeric marker genes the said polynucleotides may also further comprise elements such as enhancers, scaffold attachment regions (SARS or MARS) and introns. Various intron sequences such as the maize adh1 intron 1 have been shown to enhance expression when included into the 5' untranslated region of genes and, optionally, are used in the chimeric genes of the current invention.

Plants which have been transformed according to the invention so as to exhibit the desired male/female sterility characteristics may also have been transformed with a polynucleotide which comprises regions encoding proteins capable of conferring upon plant material containing it at least one of the following agronomically desirable traits: resistance to insects, fungi, viruses, bacteria, nematodes, stress, dessication, and herbicides.

Herbicide resistance conferring genes may, for example, be selected from the group encoding the following proteins: glyphosate oxidase (GOX), EPSP synthase, phosphinothricin acetyl transferase (PAT), hydroxyphenyl pyruvate dioxygenase (HPPD), glutathione S transferase (GST), cytochrome P450, Acetyl-CoA carboxylase (ACCase), Acetolactate synthase (ALS), protoporphyrinogen oxidase (PPO), dihydropteroate synthase, polyamine transport proteins, superoxide dismutase (SOD), bromoxynil nitrilase, phytoene desaturase (PDS), the product of the tfdA gene obtainable from *Alcaligenes eutrophus*; and known mutagenised or otherwise modified variants of the said proteins. The skilled man will recognise the need to close such genes, and the promoters which drive their expression, carefully, having regard to the nature of the enzyme he uses to convert the non-phytoxin substance. In the case that the polynucleotide provides for multiple herbicide resistance such herbicides may be selected from the group consisting of a dinitroaniline herbicide, triazolo-pyrimidines, a uracil, a phenylurea, a triketone, an isoxazole, an acetanilide, an oxadiazole, a triazinone, a sulfonanilide, an amide, an anilide, an isoxaflutole, a fluorochloridone, a norflurazon, and a triazolinone type herbicide and the post-emergence herbicide is selected from the group consisting of glyphosate and salts thereof, glufosinate, asulam, bentazon, bialaphos, bromacil, sethoxydim or another cyclohexanedione, dicamba, fosamine, flupoxam, phenoxy propionate, quizalofop or another aryloxy-phenoxypropanoate, picloram, fluormetron, butafenacil, atrazine or another triazine, metribuzin, chlorimuron, chlorsulfuron, flumetsulam, halosulfuron, sulfometron, imazaquin, imazethapyr, isoxaben, imazamox, metosulam, pyrithrobac, rimsulfuron, bensulfuron, nicosulfuron, fomesafen, fluoroglycofen, KIH9201, ET751, carfentrazone, mesotrione, sulcotrione, paraquat, diquat, bromoxynil and fenoxaprop.

In the case that the polynucleotide comprises sequences encoding insecticidal proteins, these proteins may be selected from the group consisting of crystal toxins derived from Bt, including secreted Bt toxins such as those known as "VIP"; protease inhibitors, lectins and Xenhorabdus/Photorhabdus toxins. The fungus resistance conferring genes may be selected from the group consisting of those encoding known AFPs, defensins, chitinases, glucanases, and Avr-Cf9. Particularly preferred insecticidal proteins are cryIAc, cryIAb, cry3A, Vip 1A, Vip 1B, Vip3A, Vip3B, cysteine protease inhibitors, and snowdrop lectin. In the case that the polynucleotide comprises bacterial resistance conferring genes these may be selected from the group consisting of those encoding cecropins and techyplesin and analogues thereof. Virus resistance conferring genes may be selected from the group consisting of those encoding virus coat proteins, movement proteins, viral replicases, and anti-sense and ribozyme sequences which are known to provide for virus resistance; whereas the stress, salt, and drought resistance conferring genes may be selected from those that encode Glutathione-S-transferase and peroxidase, the sequence which constitutes the known CBF1 regulatory sequence and genes which are known to provide for accumulation of trehalose.

Polynucleotides used in accordance with the present invention may have been "modified" to enhance expression of the protein encoding sequences comprised by them, in that mRNA instability motifs and/or fortuitous splice regions may have been removed, or crop preferred codons may have been used so that expression of the thus modified polynucleotide in a plant yields substantially similar protein having a substantially similar activity/function to that obtained by expression of the protein encoding regions of the unmodified polynucleotide in the organism in which such regions of the unmodified polynucleotide are endogenous. The degree of identity between the modified polynucleotide and a polynucleotide endogenously contained within the said plant and encoding substantially the same protein may be such as to prevent co-suppression between the modified and endogenous sequences. In this case the degree of identity between the sequences should preferably be less than about 70%. In addition the sequence around a translational start position may be modified such that it is "Kozack preferred". What is meant by this is well known to the skilled man.

The invention still further includes morphologically normal conditionally fertile whole plants which result from the crossing of plants which have been regenerated from material which has been transformed with the nucleic acid in accordance with the present invention and which therefore provides fopr such a trait. The invention also includes progeny of the resultant plants, their seeds and parts.

Plants of the invention may be selected from the group consisting of field crops, fruits and vegetables such as canola, sunflower, tobacco, sugar beet, cotton, maize, wheat, barley, rice, sorghum, mangel worzels, tomato, mango, peach, apple, pear, strawberry, banana, melon, potato, carrot, lettuce, cabbage, onion, soya spp, sugar cane, pea, field beans, poplar, grape, citrus, alfalfa, rye, oats, turf and forage grasses, flax and oilseed rape, and nut producing plants insofar as they are not already specifically mentioned, their progeny, seeds and parts.

Particularly preferred such plants include wheat, barley, oats, rice, maize, millet and sorghum.

The invention still further provides a preferred method of producing hybrid wheat seed which comprises the steps of
 (i) transforming plant material with a polynucleotide or vector which comprises a gene conferring male sterility conditional upon exogenous application of a pro-herbicide or other non-phytotoxic substance;
 (ii) selecting the thus transformed material; and
 (iii) regenerating the thus selected material into morphologically normal conditionally male-sterile whole plants.
 (iv) breeding a homozygous conditionally male-sterile female parent line (v) transforming plant material with a polynucleotide or vector which comprises a gene conferring female sterility conditional upon exogenous application of the same pro-herbicide or non-phytotoxic substance as in (i);
(vi) selecting the thus transformed material; and
(vii) regenerating the thus selected material into morphologically normal conditionally female-sterile whole plants
(viii) Breeding a homozygous conditionally female-sterile male parent line
(ix) Interplanting said conditionally-sterile male and female parent lines at such a ratio as to ensure efficient pollination
(x) Applying said pro-herbicide or other non-phytotoxic substance to the interplanted parent lines at such a dose and stage in development as to minimise self-fertilisation
(xi) Harvesting hybrid wheat seed from the interplanted parent plants The current invention also provides variants of the above method wherein the male parent is female sterile by any means, the female parent is male sterile by any means, male and female parent lines are conditionally sterile dependent upon the application of different pro-herbicides both of which are applied, and the crop is other than wheat.

The present invention also includes a diagnostic kit comprising means for detecting the proteins, or DNA sequences encoding them, which are present in plants produced in accordance with the present inventive method and therefore suitable for identifying tissues or samples which contain these. The DNA sequences can be detected by PCR amplification as is known to the skilled man—based on primers which he can easily derive from the enzyme encoding sequences which are disclosed or mentioned in this application. The enzymes per se can be detected by, for example, the use of antibodies which have been raised against them for diagnostically distinguishing the antigenic regions which they contain.

The present invention also provides a method of producing enantiomerically pure D-Phosphinothricin (D-PPT), comprising the steps of:
(a) Providing cells which contain an enzyme capable of selectively N-acylating PPT;
(b) Growing said cells in a medium which contains D-L PTT to produce conditioned medium;
(c) Separating the cells from the conditioned medium of (b);
(d) Optionally extracting the conditioned medium with a non-aqueous, non miscible solvent, at various pHs, so that the PPT containing fraction is separated from the fraction that contains molecules more water soluble than is PPT;
(e) Optionally admixing with the conditioned or PPT-containing extracted media of step (d) a cation exchange resin in its protonated form, in an amount, and at pH, sufficient to absorb a substantial proportion of the cations—other than PTT, from the medium;
(f) Admixing with the conditioned medium, extracted medium or medium to result from step (e) a cation exchange resin in its protonated form, in an amount, and at a pH, sufficient to bind the bulk of the PPT in the medium;
(g) Harvesting the cation ion exchange resin from step (f) to which the PPT is bound and selectively eluting PPT from it using an eluting medium having a sufficient pH and ionic strength, with the proviso that the pH of the said eluting medium is not so low as to cause racemisation of the thus eluted PPT.

In respect of the transformation of plant material, those skilled in the art will recognise that although particular types of target material (e.g. embryogenic cell suspension culture or de-differentiating immature embryos) and particular methods of transformation (e.g. using Agrobacterium or particle bombardment) are specified in the examples below, the present invention is not limited to these particular embodiments and such target materials and methods may be used interchangeably. Furthermore the term "plant cells" as used throughout this description of the invention can refer to isolated cells, including suspension cultures as well as to cells in an intact or partly intact tissue such as embryo, scutella, microspore, microspore-derived embryo or somatic cells from plant organs. Similarly, although the specific examples are limited to maize and wheat, the invention is equally applicable to a broad range of agricultural crops which can be transformed using suitable methods of plant cell transformation.

The present invention will be further apparent from the following non-limiting examples taken in conjunction with the associated Sequence Listing and Drawings.

SEQ ID NO: 1 shows a DNA sequence, isolated from *Synechocystis* sp. which encodes an enzyme (depicted as SEQ ID NO: 2) having the activity of an esterase B.

SEQ ID NO: 3 shows a DNA sequence, isolated from *Neurospora crassa* which encodes an enzyme (depicted as SEQ ID NO: 4) having the activity of an acyl-methylacyl-CoA racemase sequence.

SEQ ID NO: 5 and 6 depict the PCR primers used to obtain the TA29 promoter region.

SEQ ID NO: 7 depicts a DNA sequence, isolated from *Rhodotorula gracilis* which encodes an enzyme having the activity of a D-amino acid oxidase.

SEQ ID NO: 8 and 9 depict degenerate oligos used to provide variant D-amino oxidase.

SEQ ID NO: 10 and 11 depict motifs where alternative amino acids may substituted in order to provide variant D-amino acid oxidases.

FIG. 1 is a schematic representation of a construct for tobacco transformation having *Rhodotorula* D-amino acid oxidase under operable control of the stig 1 promoter region. The components indicated are LB (left border sequence), AOPR1 (AoPR1 promoter), PSTIG1 (EMBL accession no. X77823), RGDAO (OPT) (SEQ ID NO: 7), PC PROMOTER (EMBL accession no. X16082), PAT (EMBL accession no. A02774), NOS (nos terminator obtained from EMBL accession no. ATU237588) and RB (right border sequence).

Figure 1:
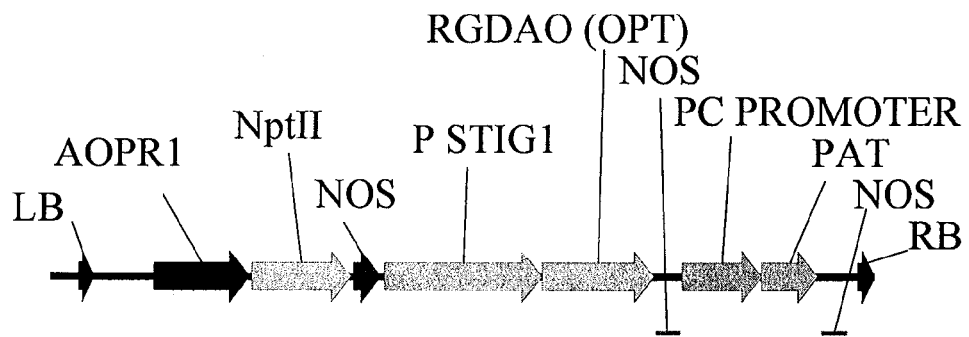

General molecular biology methods are carried out according to well established methods.

For the most part the following examples each comprise multiple exemplifications of the current invention. Where the term 'promoter region of a gene' is used this is taken to mean DNA sequences which comprise the promoter, sequences upstream of the promoter and also, optionally, all or part of the DNA sequence encoding the 5' untranslated leader region of the mRNA.

EXAMPLE 1

Tobacco Plants which are Conditionally Female Sterile Dependent Upon Exogenous Application of D-Phosphinothricin or D Alanine or D Leucine or D Methionine or D Asparagine or D-Aspartate or D-Glutamate The DNA sequence encoding the D-amino acid oxidase protein sequence Q99042 (Swissprot) within the EMBL sequence Z50019 is either obtained by RT-PCR from *Trigonopsis variabilis* mRNA or is obtained synthetically. Alternatively the DNA sequence encoding the D-amino acid oxidase protein sequence P80324 (Swissprot) within the EMBL sequence A56901 is either obtained by RT-PCR from *Rhodosporidium tolruloides* (*Rhodotorula gracilis*) mRNA or is obtained synthetically (which makes it easier to control which internal restriction enzyme sites are present and to create flanking sites to facilitate cloning) as, for example, SEQ ID #7 which is designed to account for plant (in this case wheat) codon usage and to minimise DNA features potentially inimicable to expression. Alternatively, the DNA sequence (e.g derived from EMBL Accession X95310) encodes a 'D-aspartate oxidase' such as P31228 (Swiss Prot) and, again, is synthesised to account for plant codon usage and to minimise features inimicable to expression. Alternatively D-amino acid oxidase encoding sequences obtained are the same as in example 2. Flanking PCR-primer and synthetic DNA sequences are designed to place useful unique restriction sites for cloning. Preferably and in the case where the oxidase coding sequence does not contain confounding internal sites, an Nco1 or Nde1 site is placed at the 5' end to facilitate the cloning of in-frame fusions with sequences added 5' to the ORF such as chloroplast transit peptide encoding sequences. In some variants of the example the D-amino acid oxidase (in some variants named 'D aspartate oxidase') gene is cloned in such a way that the terminal 3 amino acids are truncated and the encoded enzyme is therefore no longer peroxisomally targeted. In an additional series of variants of the method the gene is engineered by PCR so as to encode the *Rhodotorula gracilis* D amino acid oxidase with alternative amino acids at positions 213 and 238 and, in particular, with an arginine, serine, cysteine, lysine, asparagine or alanine replacing the methionine at position 213 and/or a histidine, serine, cysteine, asparagine or alanine replacing the tyrosine at position 238. The methionine at the '213' position is identified as the M in the native protein sequence motif RCTMDSS (SEQ ID #10). The tyrosine at position 238 is identified as the 'Y' within the native protein sequence motif GGTYGVG (SEQ ID #111). These variants of the D amino acid oxidase from *Rhodotorula* or the 'D-aspartate oxidase' are used when female sterility is to be made conditional upon the application of D-aspartate, D-glutamate or D-phosphinothricin.

Restriction sites can be placed upstream of the ATG translational start site intervening sequences to conform to plant translational concensus sequences such as according to Kozak.

The 'delta S13 promoter' is a promoter region useful for obtaining preferential expression in female flower parts. This comprises a region −339 to −79 from the SLG13 promoter region fused to the −46 to +8 of the CMV 35S core promoter (Dzelkalns et al (1993) Plant Cell, 5, 833-863). This S13 promoter region is cloned into bluescript sk which plasmid is then further restricted and ligated with restriction fragments comprising the nos 3' transcriptional terminator region and one or other of the amino acid oxidase coding sequences so as to create a 'delta S13-D-amino acid oxidase-Nos terminator' expression cassette within a bluescript sk plasmid. This is then suitably restricted out as, for example, an EcoR1 fragment and, as such ligated back into a suitable site in a vector such as pBIN19 (Bevan (1984) Nucleic Acids Res.) or pCIB200 or pCIB2001 (WO 98/39462) for use for transformation using *Agrobacterium*. As described in WO 98/39462 pCIB200 contains the following unique polylinker restriction sites: EcoR1, Sst1, Kpn1, BglII, Xba1 and SalI. PCIB2001 contains an insertion in the polylinker which adds further unique restriction sites including MluI, BclI, AvrII, ApaI, HpaI and StuI. PCIB200 and pCIB2001 also provides selectable marker genes for plant and bacterial selection on kanamycin, left and right T-DNA borders, the RK2-derived trfA function for mobilization between *E. coli* and other hosts and the oriT and oriV functions from RK2. Alternatively the binary vector pCIB10 which incorporates sequences from the wide host range plasmid pRK252 is used (Rothstein et al (1987) Gene 53, 153-161) or one of its derivatives which incorporates both kanamycin resistance genes and the hygromycin phosphotransferase gene such as pCIB715 is used (Gritz et al (1983) Gene 25, 179-188).

Alternatively the ~1.6 kb Stig1 promoter region (derived from EMBL accession X77823) is used. For example the coding region of the GUS gene in the stig1-GUS construct described by Goldman et al (1994) in EMBO J., 13, 2976-2984, is replaced with the DNA sequence encoding either the P80324 or Q99042 coding sequences using suitable restriction enzymes and the resultant stig1-D-amino acid oxidase expression construct cloned into in a suitable vector such as pCIB200 at a position upstream of a 3' terminator sequence adjacent to a suitable marker gene and between T-DNA border sequences.

In a further particular example the T-DNA insert within the binary vector is constructed according to FIG. 1. A construct comprising the synthetic DNA sequence (SEQ ID #7) encoding *Rhodotorula gracilis* D-amino acid oxidase under operable control of the stig1 promoter region and also the DNA sequence (A02774) encoding L-phosphinothricin N-acetyl transferase (PAT) under operable control of the pea plastocyanin promoter region is cloned into a site between the LB/npt II gene and the R B of the T-DNA of the binary vector. In brief, sequence ID #7 is cloned into plasmid pFse4-Stig1nos (described in WO9942598) behind the Stig1 promoter and in front of the nos terminator region (comprised within EMBL: ATU237588) as an NcoI/PstI fragment. The pea plastocyanin promoter region (derived from EMBL Accession number X16082) is obtained from pea genomic DNA by PCR and cloned in front of the PAT gene/nos terminator. The resultant PC-PAT-nos cassette is cloned behind the Stig1-RGDAMOX-nos as a NotI fragment and this whole two gene construct is transferred to a binary vector (pVB6, a Bin19 derivative) as an FseI fragment.

Figure 2:
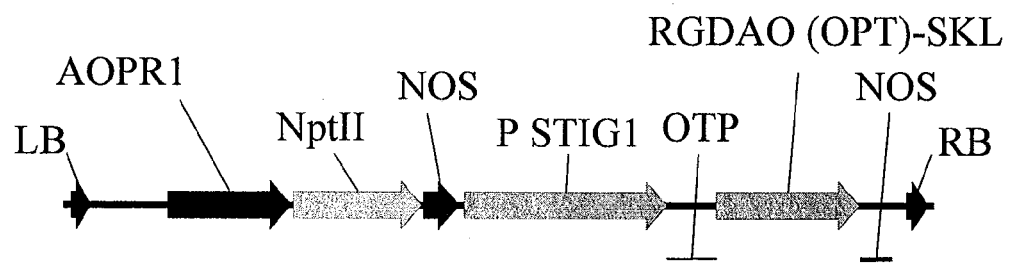
FIG. 2 is a schematic representation of a construct for tobacco transformation where the *Rhodotorula* D-amino acid oxidase coding sequence is truncated by 3 codons at the 3' terminus and, at the 5' terminus (RGDAO (OPT)-SKL), is fused to a region encoding an optimised transit peptide (FR2673643).

In a further variant of the method the construct used is according to the schematic representation in FIG. 2. The *Rhodotorula* D-amino acid oxidase coding sequence, SEQ ID#7, optionally site-directed mutated to encode the M213R form, is truncated by 3 codons at the 3' terminus and, at the 5' terminus, is cloned to place it immediately downstream of a region encoding a chloroplast transit peptide so that a chloroplast transit peptide/D-amino acid oxidase fusion protein is encoded. The chloroplast transit peptide encoding sequence is derived from the *Arabidopsis* gene encoding the small subunit of EPSP synthase (Klee et al 1987 in Mol. Gen. Genet., 210, 437). Optionally this is modified to include an SphI site at the CTP processing site thereby replacing the Glu-Lys at this location with Cys-Met (SEQ in FIG. 9. of WO 92044490). Correspondingly, an SPh 1 site may be engineered at the N-terminus of the D-amino acid oxidase coding sequence (converting the amino acid following the methionine to a leu). Alternatively the chloroplast transit peptide encoding sequence is derived from the Petunia gene encoding EPSP synthase (FIG. 11 of WO 92044490). Alternatively the chloroplast coding sequence is any one of a large number of possibilities including those derived from genes encoding the small subunit of Rubisco and including the so-called 'optimized' chimeric transit peptide sequence (FR 2673643). In all cases, rather than rely on subcloning, the whole desired DNA sequence encoding the chloroplast transit peptide/*Rhodotorula* D-amino acid oxidase fusion polypeptide may simply be obtained synthetically. This sequence is cloned into a site downstream of the stig1 promoter region and upstream of an (e.g nos) terminator sequence within a suitable vector (e.g. replacing the GUS coding sequence in the vector containing the stig1→GUS construct described by Goldman et al (1994) in EMBO J., 13, 2976-2984). The whole gene expression construct is then cloned into a suitable site between the right and left borders of the T-DNA of a PVB6 vector.

Tobacco leaf discs are transformed with the recombinant binary vectors using methods similar to those described in Horsch et al (1985) Science, 227, 1229-1231 Many variations of the method may be used. The binary vector can be transformed into, for example, *Agrobacterium tumefaciens* strain LBA 4404 using the freeze thaw method of transformation. Tobacco transformation and whole plant regeneration is performed using *Nicotiana tabacum* var. *Samsun* according to protocols described by Draper et al (Plant Genetic Transformation, Blackwell Sci. Pub. 1989). Transformation events are selected on MS-media containing kanamycin or other suitable antibiotic. The presence of integrated transgenes is confirmed by PCR. Plants are regenerated and allowed to reach maturity and selfed on to produce seed. Northern and/or Western analysis is used to confirm tissue-specific expression of the D-amino acid oxidase genes. The plants are self-fertile but have the condition of conditional female sterility. Seeds of the T1 generation are planted out. Once plantlets have grown to a sufficient size they are tested by PCR for the presence of transgene. PCR positive plants are transferred to the greenhouse. These plants are fully fertile in the absence of exogenously applied proherbicide. A subset of these (putatively) conditionally sterile plants are treated with D-phosphinothricin or D-alanine or D leucine or D asparagine or D methionine or D-aspartate or D-glutamate in various amounts and at varying growth stages. Such treatments are carried out on the T1 plants confirmed as PCR positive for the D-amino acid oxidase gene, or, equally, such treatments are carried out directly on plants of the To generation (which are vegetatively cloned so that untreated clones of each event may be set aside for seed production). The observed fertility is then used as a basis to select suitable plant lines exhibiting the clearest conditional sterility phenotype. For example these amino acids are pure D enantiomers or, alternatively, are DL racemates. For example, they are applied as a foliar spray, prior to or during the early stages of flower formation, at rates usually between 0.25 and 20 kg/ha. Amino acids which may crystallise out of solution on the leaves following foliar application may be redissolved and remobilised for leaf uptake by further applications of water as a spray mist. Amino acids are, for example, also applied as a root drench and optionally, further applied as ~50 ul of a 10-200 mM solution flooded directly into the buds of emerging florets. Pollen from the treated plants is collected and viability is tested. Plants are obtained which produce relatively little or no seed after treatment with D phosphinothricin or D alanine or D leucine or D asparagine or D methionine or D aspartate or D glutamate but which, nevertheless, under the same treatment conditions do produce near normal levels of viable pollen. Control plants are both transgenic and non-transgenic and are grown under identical conditions and under an identical regime of physical treatments except that treatment solutions are either water or an equivalent concentration of pure L-amino acid.

In one variant of the method, the amino acid applied is racemic DL phosphinothricin. In this case, the DNA construct used for transformation comprises, in addition to the DNA sequence encoding a D-amino acid oxidase under operable expression control of a tissue specific female floral promoter region such as 'stig 1', also a DNA sequence (EMBL: A02774) a 'PAT' gene under operable control of a promoter region such as the region 5' of the translational start of the plastocyanin gene of the *Pisum sativum* plastocyanin gene (EMBL accession number X16082). For example, the construct is the same as depicted in FIG. 1 except that the DNA sequence encoding D-amino acid oxidase is site-specifically mutated so that the M213R form of the enzyme is encoded. The plastocyanin promoter region provides for preferential expression in the green tissues of the plant. It is found, unexpectedly, that such a promoter which, unlike for example, the 35S promoter region, is substantially expressed only in certain tissues of the plant and most notably in green tissues, does, nevertheless, when used in combination with the PAT gene provide for substantially complete reproductive tolerance to the herbicide DL PPT even at rates in excess of 2 kg/ha. Furthermore, in the absence of any suitable heterologous D-amino acid oxidase or similar D to L converting activity being co-expressed in the floral tissues, the plastocyanin/PAT gene combination provides essentially complete reproductive tolerance with no significant loss of yield despite the PAT expression level being low or non-existent in many of the critical floral tissues when expressed under control of this promoter region. Thus, in this variant of the example, the non-phytotoxic substance D phosphinothricin is applied in its least costly and most readily available form as the commercial herbicide DL phosphinothricin racemate. At appropriate spray timings and rates between 250 g/ha and 5 kg/ha of DL phosphinothricin the treated plants are not visibly damaged but are rendered conditionally female sterile whilst remaining of normal or near-normal male fertility.

EXAMPLE 2

Tobacco Plants which are Conditionally Male Sterile Dependent Upon Exogenous Application of D-Phosphinothricin or D Alanine or D Leucine or D Methionine or D Asparagine or D-Aspartate or D-Glutamate The DNA sequence encoding the D-amino acid oxidase protein sequence Q9HGY3 (Sptrembl) within the EMBL sequence AB042032 is either obtained by RT-PCR from *Candida boidini* mRNA or is obtained synthetically. Alternatively the DNA sequence encoding the D-amino acid oxidase protein sequence P24552 (Swissprot) within the EMBL sequence D00809 is either obtained by RT-PCR from *Fusarium solani* mRNA or is obtained synthetically. Flanking PCR-primer or synthetic DNA sequences are designed to place useful unique restriction sites for cloning. Preferably and in the case where the oxidase coding sequence does not contain confounding internal sites, an Nco1 or Nde1 site is placed at the 5' end to facilitate the cloning of in-frame fusions with sequences added 5' to the ORF. Alternatively, where restriction sites are placed upstream of the ATG translational start site intervening sequences are designed to conform to plant translational concensus sequences such as according to Kozak. Alternatively D-amino acid oxidase encoding sequences obtained are the same as in example 1. Again, as in the previous example, where sterility is to be made dependent upon the application of D-aspartate, D glutamate or D phosphinothricin then, preferably, D-amino acid oxidases are variants at amino acid positions 213 and/or 238.

The TA29 promoter region (Kriete et al (1996) Plant J., 9, 808-818) is cloned from tobacco genomic DNA by PCR using the primers 5'-AACTGCAGCTTTTTGGTTAGC-GAATGC-3' (SEQ ID #5) and 5'-CAGACTAGTTT-TAGCTAATTTCTTTAAGTAAAAAC-3' (SEQ ID #6). Through a series of restriction and subcloning steps the PCR fragment so obtained is placed upstream of the D-amino acid oxidase coding sequence and a nos transcriptional terminator is added 3' of the coding region. The resultant TA29-D-amino acid oxidase-nos terminator expression cassette is then cloned, obtained as a suitable restriction fragment and cloned into a binary vector as in Example 1. As in example 1, where sterility is to made conditional upon application of D-aspartate, D-glutamate or D phosphinothricin it is preferred that variants of *Rhodotorula gracilis* D-amino acid oxidase be used with mutations at positions 213 and/or 238.

Alternatively, any of the above D-amino acid oxidase coding sequence regions are cloned as a suitable restriction fragment (for example BamH1, Bgl/II where synthetic variants of coding sequences are designed so as to remove internal restriction sites) and fused to the CaMv 35S promoter and the nopaline synthase terminator regions by insertion into (for example) the BamH1 site of the binary vector pROK1 (Baulcombe et al (1986) Nature, 321, 446-449) in a sense configuration. The EcoR1-BamH1 fragment carrying the 35S promoter region is then excised and replaced with an EcoR1-BamH1 fragment from pAP30 (Kriete et al (1996) The Plant Journal 9, 809-818) carrying the TA29s promoter region fragment (−810 to +54). The resultant vectors can be termed pGKTA29_Q99042, pGKTA29_P80324, pGKTA29_Q9HGY3 and pGKTA29_P24552 etc. according to the protein sequence encoded.

Tobacco plant material is transformed, via *Agrobacterium*, with vector and transgenic plants are regenerated in a similar manner to that described in the previous example. The plants produced are self-fertile but are conditionally male sterile. Seeds of the T1 generation are planted out into soil. Once plantlets have grown to a sufficient size they are tested by PCR for the presence of transgene. PCR positive plants are transferred to the greenhouse. These plants are fully fertile in the absence of exogenously applied proherbicide. A subset of these putatively conditionally sterile T1 plants, or, alternatively plantlets of T0 'events' (direct regenerants from transformation) are treated with D-phosphinothricin or D alanine or D leucine or D methionine or D asparagine or D-aspartate or D-glutamate in various amounts and at varying growth stages. Where To plants are treated they are vegetatively cloned so that untreated siblings of the events are set aside for seed production. The observed fertility is then used as a basis to select suitable plant lines exhibiting the clearest conditional sterility phenotype. For example these amino acids are pure D enantiomers or, alternatively, are DL racemates. For example, they are applied as a foliar spray, prior to or during the early stages of flower formation, at rates usually between 0.25 and 20 kg/ha. Amino acids which may crystallise out of solution on the leaves following foliar application may be redissolved and remobilised for leaf uptake by further applications of water as a spray mist. Amino acids are, for example, also applied as a root drench and optionally, further applied as a 10-200 mM solution directly into the buds of emerging florets.

Pollen from the treated plants is collected and viability is tested. Plants are obtained which shed no or relatively little pollen and/or pollen which is not viable. Pollen collected from some of the treated plants is tested and found to be malformed and non-viable. However, such male infertile plants remain female fertile and produce (hybrid) seed when pollinated with pollen collected from other, untreated non-transgenic or conditionally female-sterile tobacco plants. Control plants are both transgenic and non-transgenic and are grown under identical conditions and under an identical regime of physical treatments except that treatment solutions are either water or an equivalent concentration of pure L-amino acid.

Analagous to example 1, in one variant of the example, the amino acid applied is racemic DL phosphinothricin. In this case the DNA construct used for transformation comprises, in addition to the DNA sequence encoding a D-amino acid oxidase under operable expression control of a tissue specific male floral promoter region such as 'TA 29', also a DNA sequence encoding a phosphinothricin N-acetyl transferase gene such as the 'PAT' gene under operable control of a promoter region such as that from the plastocyanin gene (in this case the region from the *Pisum sativum* plastocyanin gene). At appropriate spray timings and rates between 250 g/ha and 5 kg/ha of DL phosphinothricin the treated plants are not visibly damaged but are rendered conditionally male sterile whilst remaining of normal or near-normal female fertility.

EXAMPLE 3

Chimeric Genes Preferentially Expressed in Male Reproductive Structures and Encoding Enzymes Capable of Hydrolysing Imazamethabenz Methyl or Flamprop M Methyl or Flamprop M Isopropyl to their Respective Carboxylic Acids The DNA sequence encoding the carboxylesterase protein sequence Q01470 (Swissprot) within the EMBL sequence M94965 is either obtained by PCR from genomic DNA of *Arthrobacter oxydans* or is obtained synthetically. Alternatively the DNA sequence encoding the carboxylesterase protein sequence P37967 (Swissprot) within the EMBL sequence BS06089 is either obtained by PCR from *Bacillus subtilis* genomic DNA or is obtained synthetically. Alternatively the DNA sequence encoding the carboxylesterase protein sequence P40363 (Swissprot) within the EMBL sequence Z34288 is either obtained by RT-PCR from *Saccharomyces cerevisiae* mRNA or is obtained synthetically. Flanking PCR-primer or synthetic DNA sequences are designed to place useful unique restriction sites for cloning. Preferably and in the case where the carboxylesterase coding sequence does not contain confounding internal sites, an Nco1 or Nde1 site is placed at the 5' end to facilitate the cloning of in-frame fusions with sequences added 5' to the ORF. Alternatively, where restriction sites are placed upstream of the ATG translational start site intervening sequences are designed to conform to plant translational concensus sequences such as according to Kozak.

Plasmid pGK73 carries the TA29s promoter region EcoR1-BamH1 fragment from −810 to +54 (Kriete et al (1996), 9, 809-818). This restriction fragment or a similar suitable PCR-generated fragment is cloned, preferably as an in-frame fusion, at a position upstream of the DNA sequence encoding either carboxylesterase Q01470 or P37967 into bluescript sk.

Using a suitable series of restriction, ligation and subcloning steps a nos transcriptional terminator is added 3' of the coding region to generate, according to the coding sequence, alternative expression cassettes of the type TA29-carboxylesterase-nos in Bluescript sk plasmids, pBLTA_Q01470, pBLTA_P37967 and pBLTA_P40363.

In a further example, the anther specific SGB6 promoter region seq ID number 1 of U.S. Pat. No. 5,470,359 is used. For example, pSGBNE1 containing a 3 kb genomic EcoR1-Nhe1 subcloned fragment from pSGB6g1 (U.S. Pat. No. 5,470,359) is further subcloned to place a 1558 bp ApaII/Xba1 fragment blunt cloned into bluescript ks at the SmaI site. As before, through further restriction and cloning steps this fragment is fused in frame upstream of either the P37967, Q01470 or P40363 DNA coding sequences. Again a nos terminator is added 3' of the coding region to create, alternative, Bluescript sk plasmids, pBLB6_Q01470, pBLB6_P37967 and pBLB6_P40363 comprising the alternative SGB6-carboxylesterase-nos expression cassettes.

In a similar set of examples the RA8 anther-specific promoter region from rice (EMBL/genbank accession AF042275; Jean Js et al (1999) PMB, 39, 35-44) is similarly also fused at a site in-frame and upstream of one or other of the DNA sequences encoding carboxylesterase and a nos 3' terminator to comprise alternative RA8-carboxylesterase-nos expression cassettes in a series of bluescript sk vectors, pBLRA8_Q01470, pBLRA8_P37967 and pBLRA8_P40363.

EXAMPLE 4

Chimeric Genes Preferentially Expressed in Female Reproductive Structures and Encoding Enzymes Capable of Oxidising D Phosphinothricin and/or D Alanine and/or D Leucine and/or D Methionine and/or D Asparagine and/or D-Aspartate and/or D-Glutamate DNA sequences encoding D-amino acid oxidase protein sequences are obtained as described in Examples 1 and 2.

The genomic clone pSH64 was deposited under the terms of the Budapest treaty on Feb. 27, 1998 with NRRL and assigned the number NRRL B-21920. It was detected as a genomic clone hybridising to the silk-specific cDNA clone B200i4-2 (WO 98/39462). Chimeric genes which are expressed preferentially in female reproductive structures are constructed as follows. A bluescript ks-derived plasmid similar to pSH70 having an 'empty' expression cassette comprising, from 5' to 3', the B200i 5' promoter region consisting of nucleotides 1-3790 of SEQ ID No 11 of WO 98/39462, a BamH1 site and the B200i 3' untranslated terminator region comprising nucleotides 4427-6397 of sequence ID No. 11 of WO 98/39462 is constructed as described in WO 98/39462. Using a partial BamH1 digestion or, alternatively by further subcloning, PCR and ligation steps alternative D-amino acid oxidase coding sequences are ligated into the position at or adjacent to the BamH1 site such that they are immediately 3' of the B200i promoter region and 5' of the B200i terminator region. Accordingly, a series of bluescript vectors pBLB200_Q99042, pBLB200_P80324, pBLB200_Q9HGY3 and pBLB200_P24552 encoding the alternative B200i-D-amino acid oxidase-B200i expression cassettes are created.

Alternatively, as described in WO 98/39462, a Pst I/Nco I fragment of the 5' promoter region of the P19 gene is excised from the genomic clone X2-1 which was deposited under the terms of the Budapest treaty on Feb. 27, 1998 at NRRL and assigned accession number B-21919. The Nco I site at nucleotide 1088 of SEQ ID No 14 of WO 98/39462 corresponds with the ATG translational start of the P19 gene. Using appropriate subcloning, restriction, ligation and PCR steps this fragment is ligated to form a in-frame fusion with one or other of the DNA sequences encoding D-amino acid oxidase and a nos terminator sequence is added 3' of the coding sequence. Accordingly, a series of bluescript vectors pBLP19_Q99042, pBLP19_P80324, pBLP19_Q9HGY3 and pBLP19_P24552 etc. encoding the alternative P19-D-amino acid oxidase-nos expression cassettes are created. Alternatively, using similar standard methods, similar plasmids are obtained having the 5' promoter region (comprising some or all of nucleotides 1-3987 of SEQ ID No 2 of WO 98/39462) of the P26 gene in place of the P19 promoter region. The genomic P26-A4 clone, pCIB10302 deposited under the terms of the Budapest Treaty on Jan. 21, 1997 with the Agricultural Research Service patent culture collection, (NRRL) accession number NRRL B-21655 is subcloned as described in WO 98/39462. Accordingly, a series of bluescript vectors pBLP26_Q99042, pBLP26_P80324, pBLP26_Q9HGY3 and pBLP26_P24552 encoding the alternative P19-D-amino acid oxidase-nos expression cassettes are created.

EXAMPLE 5

Chimeric Genes Preferentially Expressed in Male Reproductive Structures and Encoding Enzymes Capable of Oxidising D Phosphinothricin and/or D Alanine and/or D Leucine and/or D Methionine and/or D Asparagine and/or D-Aspartate and/or D-Glutamate DNA sequences encoding D-amino acid oxidase protein sequences are obtained as described in Examples 1 and 2.

Plasmid pGK73 carries the TA29s promoter region EcoR1-BamH1 fragment from −810 to +54 (Kriete et al (1996), 9, 809-818). This restriction fragment or a similar suitable PCR-generated fragment is cloned, preferably as an in-frame fusion, at a position upstream of the DNA sequence encoding the D amino acid oxidase into bluescript sk. Using a suitable series of restriction, ligation and subcloning steps a nos transcriptional terminator is added 3' of the coding region to generate, according to the coding sequence, alternative expression cassettes of the type TA29-D-amino acid oxidase-nos in Bluescript sk plasmids.

In a further example, the anther specific SGB6 promoter region seq ID number 1 of U.S. Pat. No. 5,470,359 is used. For example, pSGBNE1 containing a 3 kb genomic EcoR1-Nhe1 subcloned fragment from pSGB6g1 (U.S. Pat. No. 5,470,359) is further subcloned to place a 1558 bp ApaII/Xba1 fragment blunt cloned into bluescript ks at the SmaI site. As before, through further restriction and cloning steps this fragment is fused in frame upstream of the D amino acid oxidase coding sequence. Again a nos terminator is added 3' of the coding region to create, alternative, Bluescript sk plasmids, comprising the alternative SGB6-D-amino acid oxidase-nos expression cassettes.

In a similar set of examples the RA8 anther-specific promoter region from rice (EMBL/genbank accession AF042275; Jean Js et al (1999) PMB, 39, 35-44) is similarly also fused at a site in-frame and upstream of one or other of the DNA sequences encoding D-amino acid oxidase and a nos 3' terminator to comprise alternative RA8-D-amino acid oxidase-nos expression cassettes in a series of bluescript sk vectors.

EXAMPLE 6

A Pair of Complementary Constructs Useful in a Method to Provide (a) a Female Inbred Parental Line which is Conditionally Male-Sterile Dependent Upon the Application of DL Phosphinothricin and (b) a Complementary Male Inbred Parental Line which is Conditionally Female Sterile Dependent Upon the Application of DL Phosphinothricin The first DNA construct suitable for providing a female inbred parental cereal or rice plant line which is conditionally male-sterile dependent upon the application of DL phosphinothricin comprises three genes A), B) and C). A) consists of a DNA sequence encoding a PAT enzyme capable of N-acetylating L-phosphinothricin under operable control of the ~1 kb promoter region from the barley plastocyanin gene (EMBL: Z28347) and a suitable terminator region such as that from the nos or 35S gene, B) consists of a PAT encoding sequence similar to the first but this time under operable control of a tissue specific female floral promoter region (such as P19 or P26 as described in example 4) plus a suitable terminator and C) consists of a suitable DAMOX encoding sequence as described in examples 1, 2, 12 and 13, encoding, for example, a mutant form of the *Rhodotorula gracilis* D amino acid oxidase having an arginine, serine, cysteine, lysine, asparagine or alanine replacing the methionine at position 213 and/or a histidine, serine, cysteine, asparagine or alanine replacing the tyrosine at position 238 under operable control of a tissue specific male floral promoter region (such as SGB6 or RA8 as described in example 5) and a suitable terminator region. This construct is assembled using methods which are standard in the art and informed by the previous examples.

The second DNA construct suitable for providing a male inbred parental cereal or rice plant line which is conditionally female-sterile dependent upon the application of DL phosphinothricin comprises three genes A), D) and F). A) consists of a DNA sequence encoding a PAT enzyme capable of N-acetylating L-phosphinothricin under operable control of the promoter region from the barley plastocyanin gene and a suitable terminator region such as that from the nos or 35S gene, D) consists of a PAT sequence similar to the first but this time under operable control of the same tissue specific male floral promoter region (such as SGB6 or RA8 as used in example 5) as used in construct I plus a suitable terminator and F) consists of a suitable DAMOX gene as described in examples 1, 2, 12 and 13 and, for example, encoding a mutant form of the *Rhodotorula gracilis* D amino acid oxidase having an arginine, serine, cysteine, lysine, asparagine or alanine replacing the methionine at position 213 and/or a histidine, serine, cysteine, asparagine or alanine replacing the tyrosine at position 238 under operable control of the same tissue specific female floral promoter region (such as P19 or P26 as described in example 4) as used in construct 1 and a suitable terminator region. This construct is assembled using methods which are standard in the art and informed by the previous examples.

A pair of DNA constructs of this example contain, for example, the following elements
Construct 1
A=Barley plastocyanin promoter region→4 PAT encoding sequence, Nos terminator;
B=P19 promoter region→PAT encoding sequence, 35S terminator;
C=RA8 promoter region→*Rhodotorula* D-amino acid oxidase (M213R mutant) encoding sequence, Nos terminator
Construct 2
A=Barley plastocyanin promoter region→PAT encoding sequence, Nos terminator;
D=RA8 promoter region→PAT encoding sequence, 35S terminator;
E=P19 promoter region→*Rhodotorula* D-amino acid oxidase (M213R mutant) encoding sequence, Nos terminator

EXAMPLE 7

Polynucleotide Vectors for Transformation of Wheat

Examples 3, 4, 5 and 6 describe the construction of various chimeric genes in expression cassettes which are usually cloned into bluescript sk (for example, pBLRA8_Q01470, pBLRA8_P37967, pBLRA8_P40363, pBLB200_Q99042, pBLB200_P80324, pBLB200_Q9HGY3 and pBLB200_P24552 etc.). Optionally these vectors are prepared in bulk for direct DNA transformation for use with a co-bombarded selectable marker such as pSOG35 (DHFR/methotrexate) or pUbi-Hyg (hygromycin phosphotransferase/hygromycin) as described in WO 98/39462. Preferably, after bulk preparation, the vectors are linearised using a suitable restriction enzyme to remove the ampicillin resistance gene of bluescript.

Optionally, rather than use co-bombardment the said bluescript vectors are further engineered by standard methods so that they further comprise a plant selectable marker gene such as kanamycin resistance, hygromycin resistance, methotrexate resistance or glyphosate resistance gene and are used directly. In some of the foregoing examples a PAT gene is integral to the design of the vector and, in these cases, DL phosphinithricin may optionally be used for selection at some stage after transformation.

Alternatively, expression cassettes are excised within a suitable restriction fragment and cloned into pIGPD9 derived vectors (described in FIG. 12 of WO 00/66748). The use of this vector for transformation avoids transfer of antibiotic marker genes to the plant since its maintenance in bacteria relies on complementation of an auxotrophic his B *E. coli* mutant. The vector comprises a gene expressing IGPD (the hisB product) and is further engineered to comprise a plant selectable marker gene such as an EPSPS gene cloned into the Xma I site as, for example, in pZEN16i and pZEN18i of WO 00/66748. Alternatively a marker gene which provides positive selection on mannose or xylose is used (U.S. Pat. No. 5,767,378).

In particular examples of using pIGPD9 vectors, plasmids for wheat transformation are constructed. Illustrative examples are pZEN18_BLB200_Q99042 and pZEN18_BLRA8_Q01470. These are pIGPD9-derived vectors comprising the pZEN18 EPSPS gene (WO 00/66748) and, in this case, either the B200i-(Q99042)D-amino acid oxidase-B200i or the RA8-(Q01470)carboxylesterase-nos expression cassettes, respectively.

Large-scale DNA preparations for use in plant transformation are obtained using the Maxi-prep procedure (Qiagen) using protocols supplied by the manufacturer.

EXAMPLE 8

Transformation/Regeneration of Wheat with Polynucleotides Comprising Chimeric Genes Preferentially Expressed in Either Male or Female Reproductive Structures and Which Encode Enzymes Capable of Oxidising D-Phosphinothricin and/or D Alanine and/or D Leucine and/or D Methionine and/or D Asparagine and/or D-Aspartate and/or D-Glutamate In one example, immature embryos (0.75-1.0 mm in length) of genotype UC703 are plated on MS medium containing 3 mg/l 2,4-D and 3% sucrose. After approximately 4 h the embryos are plated onto MS medium containing 15% maltose, 3% sucrose and 3 mg/l 2,4-D overlaid with a filter paper supported slab of agarose containing the same components. The embryos are allowed to plasmolyze for 2-3 h before bombardment.

DNA prepared as described in example 7 and in the foregoing examples is precipitated onto micrometer size gold particles using standard procedures. Four target plates with 16 embryos per target are shot twice with a DuPont Biolistics helium device using a burst pressure of 1100 psi. Plates are shot with an 80 mesh screen in place between the carrier stage and the target. After bombardment targets are placed in the dark at 25 C for 24 h before the slabs with the embryos are laid onto plates of MS medium containing 3% sucrose and 3 mg/l 2,4-D. The individual embryos are removed from the slabs and placed directly on fresh medium of the same composition after another 48 h. Approximately 6 weeks after gene delivery the tissue is placed on MS medium with 3 mg/l 2,4-D, 3% sucrose and 0.2 mg/l of methotrexate for a 3 week period. The tissue is then placed on regeneration medium comprised of MS medium containing 1 mg/l zeatin riboside and 1 mg/l methotrexate. After 2 weeks regenerating plantlets are placed in sterile containers with half-strength MS medium containing 2% sucrose, 1 mg/l napthylacetic acid and 4 mg/l methotrexate.

In particular variants of the example the vectors comprising chimeric genes preferentially expressed in male reproductive structures are co-bombarded with alternative selectable marker genes. Thus, for example, DNA of plasmids such as pBLRA8_P24552, made analogously to Example 3 (but expressing a D-amino acid oxidase rather than a carboxylesterase sequence) under operable control of the RA8 promoter region is prepared and coated onto gold particles along with pUbiHyg (a plasmid encoding hygromycin phosphotransferase under operable control of the maize polyubiquitin promoter). In this case transformation and regeneration is carried out as described above except that, following bombardment, the regeneration media contain increasing concentrations of hygromycin between 2 and 20 mg/l.

In a further example wheat is transformed with pZEN18_BLB200_Q99042, selected using glyphosate and regenerated as described in example 15 of WO 00/66748

DNA is extracted from leaf tissues of plants derived from transformation and PCR is run for the presence of selectable marker gene and the gene encoding D amino acid oxidase. PCR positive plants are propagated. During flowering, pistils and anthers are collected and RNA is prepared. DNA expression is confirmed by Northern analysis. In addition, D-amino acid oxidase genes are expressed using pET vectors in *E. coli* and part purified. The protein bands of the expressed protein is cut out of an SDS gel and used to generate polyclonal antibodies. These antibodies are used to detect expression in flower tissues and other tissues by Western analysis.

EXAMPLE 9

A Method of Efficiently Producing Hybrid Cereal Crops Wherein DL Phosphinothricin is Applied Both for Weed Control and at the Same Time as the Chemical Hybridising Agent and Wherein the F1 Hybrid Generation of Plants Resulting from the So-Produced Hybrid Seed is Both Vegetatively and Reproductively Substantially Tolerant to the Application of DL Phosphinothricin Chemical hybridising agents are expensive. It would be desirable to use a relatively cheap substance such as a commercial herbicide as a chemical hybridising agent. This would also achieve further efficiency since weed control could be combined with chemical hybridisation. However there are a number of problems to overcome in order that this proposition be realised. Firstly, male and female parental lines would need to be established which are tolerant to the herbicide in question. Furthermore, in order to achieve the desired 'conditional' fertility in response to application of the herbicide the two lines would need to be engineered in such a way that the tolerance to the herbicide did not extend to all tissues but was expressed in a tissue specific manner so that each one of the required floral tissues remained selectively susceptible. Thus, in one line (the female parent line), the bulk of the plant plus the female tissue must be rendered tolerant whilst some critical part of the male floral tissue must remain susceptible to the application whereas in the other (the male parent line), the converse is needed with only some critical part of the female gamete forming tissue remaining susceptible. Even given that this can be achieved there remains a further problem to overcome in respect of the hybrid seed and F1 generation. Given that this generation of the crop would, necessarily, contain at least two genes capable of conferring resistance to the herbicide it would be desirable that this same herbicide could also be used for weed control in the crop. However, it is very difficult to conceive of a combination of herbicides, tissue specific promoter regions and tolerance genes that would permit this use of the same herbicide in the F1 generation. It would be likely that the hybrid crop would display vegetative tolerance but little or no grain yield after herbicide application to the F1 generation. For example, for the herbicide glyphosate the usual mechanism of resistance is the expression of a resistant form of EPSP synthase. It is difficult to identify a promoter region or combination of promoter regions that would permit sufficient expression of a R-EPSPS in all tissues and at all times other than, say, at a critical stage in the development of stamens or stigmas. The most straightforward way around this would be to use an antisense or similar approach wherein expression of the R-EPSPS is driven by a tissue non-specific/constitutive promoter and only locally and transiently suppressed in, for example, the stamens due to expression of an antisense EPSPS gene (see for example WO 9946396). However, in that case the suppression of expression in the stamen (or stigma) would be driven by a dominant gene. It is clear that, for any such mechanism, the application of the herbicide to the F1 generation would result in a sterile non-yielding crop due to the additive effects of the dominant male and female conditional sterility genes.

The current invention provides a method of overcoming the problem of enabling the use of a cheap commercial herbicide, DL phosphinothricin, as both weed control and hybridising agent in the production of hybrid cereals and which method, furthermore, provides resultant hybrid cereals or rice in which DL phosphinothricin (or L phosphinothricin) can be safely used for weed control without substantial loss of yield. As a yet further benefit, selfed seed from the F1 generation which may later arise as volunteers in subsequent crops will be easier to manage since they, themselves, will generally be sterile if sprayed with controlling amounts of DL phosphinothricin. The same will hold for the progeny of pollen outcrossing from the F1 plants to weeds (e.g red rice) or other cereals. The current invention provides genes and enzymes that convert a non-phytotoxic component, D-phosphinothricin, of a commercial herbicide formulation DL phosphinothricin, into the active L form. The PAT gene which converts L-phosphinothricin to N-acetyl L-phosphinithricin is known already and is used commercially to provide tolerance to DL phosphinothricin in crops. A further critical observation germane to the current example is that, surprisingly, wheat containing a PAT gene under operable expression control of the barley plastocyanin promoter region is found to be substantially reproductively tolerant to the application of DL phosphinothricin at rates up of at least 2 kg/ha. Thus a critical feature of the constructs described in example 6 which are used to provide the plants of the current example is that the PAT gene which provides the resistance trait is expressed under operable control of a promoter region which provides for expression in substantially only the green tissues. A characteristic of such a useful promoter region is that it should express PAT in such a way that it protects adequately all the non-green floral tissues from foliarly applied DL phosphinothricin whilst, at the same time, providing only a minimal level of PAT expression in the floral tissue itself and especially low in those parts targeted for conditional sterility. With PAT expressed under operable control of the barley plastocyanin promoter region this condition appears to be met since substantially all of the L-phosphinothricin which is sprayed enters via the leaves is intercepted and converted to non-phytotoxic N-acetyl-L-phosphinothricin before it translocated to developing floral tissues. Thus, in the current invention, the L phosphinothricin which causes the tissue selective sterility effects in the parental lines is only generated transiently and locally from phloem mobile non-phytotoxic D-phosphinothricin via D amino acid oxidase. By exactly matching the floral control elements driving expression of PAT to those elements which drive expression of D-amino acid oxidase in the complementary pair of constructs (example 6) it is ensured that, in the F1 hybrid, the transient burst of L-phosphinothricin in the target floral tissue is rapidly neutralised by a corresponding burst of PAT expression at the same time and in the same local tissue. Thus application of the herbicide induces no sterility effect in the hybrid. However, in further generations, the florally corresponding PAT and D-amino acid oxidase of the hybrid will segregate apart and thus, once again, the resulting plants will be male or female sterile upon application of controlling amounts of DL phosphinothricin.

Using the methods described in examples 7 and 8, the constructs described in example 6 are transformed into wheat or (using standard superbinary vector methods) into rice which is selected and regenerated into plantlets. T0 transformant events are selected (using clonal propagation of tillers to maintain untreated lines) and suitable events for breeding on as, alternatively, male inbred parental lines which are conditionally female sterile dependent upon the application of DL phosphinothricin or female inbred lines which are conditionally male sterile dependent upon the application of DL phosphinothricin are selected using methods essentially as described in examples 1 and 2. The best lines exhibit the best herbicide tolerance, minimum yield loss, cleanest conditional sterility phenotype etc. The alternative male parent and female parent lines are selected and, optionally, backcrossed into suitable elite lines for a number of generations. The genetic inserts in these finally selected events are fully characterized as are the genetics of the inheritance of the conditional fertility and herbicide resistance traits and the characteristics of expressed gene products.

The, thus selected, female and male parental lines are then interplanted together in suitable ratios in a field and sprayed with DL phosphinothricin at a suitable rate between 0.05 and 5 kg/ha and timing up to the period of early flowering selected to optimise the production of hybrid seed. The seed thus produced have the advantage that they will give rise to plants which not only benefit from hybrid vigour but which are also tolerant to the herbicide formulations containing DL phosphinithricin which may thus be used for weed control. The hybrid seed also have the advantage that the herbicide tolerance trait that they express will be only incompletely passed onto future selfed generations or outcrossed into related weeds. Thus, for example, the hybrid rice resulting from this invention can be grown using DL phosphinothricin as weed control agent without significant loss of yield. However future generations of red rice plants which arise as the progeny of pollen from the hybrid rice outcrossing with red rice female parents will be vegetatively tolerant to treatment with DL phosphinothricin but have reduced self-fertility (owing to the expression of a D-amino acid oxidase in the floral tissue) and thus produce little grain. Hence using hybrid rice of the current invention DL phosphinothricin may be used for weed control with much reduced future risk of grain contamination with red rice as a result of the herbicide resistance trait having outcrossed into the closely related red rice. Similarly, second generation volunteers of rice or wheat which arise from the hybrid crop will, for the most part, not produce grain after spraying with DL phosphinothricin.

EXAMPLE 10

Transformation/Regeneration of Maize with a Polynucleotide Comprising a Chimeric Gene Preferentially Expressed in Male Reproductive Tissue and which Encodes an Enzyme Capable of Hydrolysing Imazamethabenz Methyl or Flamprop Methyl or Flamprop Isopropyl to their Respective Acids RA8-carboxylesterase-nos expression cassettes are cloned into a series of bluescript sk vectors, pBLRA8_Q01470, pBLRA8_P37967 and pBLRA8_P40363 as described above. Optionally, these are combombarded with DNA comprising selection markers such as pUbiHyg or pSOG35, selected and regenerated using hygromycin or methotrexate as described, for example, in example 11 of WO 98/39462.

Alternatively, pZEN18_BLRA8_Q01470 is directly bombarded or transferred on silicon carbide whiskers into maize cells and maize plants are selected and regenerated on glyphosate as, for example, described in examples 12 and 13 of WO 00/66748.

Alternatively maize transformation is carried out using *Agrobacterium tumefaciens* containing a superbinary vector. For example, the pZEN18 expression cassette and the BLRA8_Q01470 chimeric gene is excised from, pZEN18_BLRA8_Q01470 and cloned into positions between the right and left T-DNA borders of a pSB1-derived superbinary vector through a series of subcloning and homologous recombination in a series of steps similar to those described in WO 00/66748. Plant material derived from immature embryos is infected with *Agrobacterium* containing superbinary vector comprising the glyphosate marker gene and the chimeric gene of the current invention. Plants are selected and regenerated using glyphosate as described in WO 00/66748.

DNA is extracted from leaf tissues of plants derived from transformation and PCR is run for the presence of selectable marker gene and the gene encoding carboxylesterase. PCR positive plants are propagated. During flowering pistils and anthers are collected and RNA is prepared. DNA expression is confirmed by Northern analysis. In addition, carboxylesterase genes are expressed using pET vectors in *E. coli* and part purified. The protein bands of the expressed protein is cut out of an SDS gel and used to generate polyclonal antibodies.

These antibodies are used to detect expression in flower tissues and other tissues by Western analysis.

EXAMPLE 11

Transformation of Maize Cells to a Phenotype which Exhibits Enhanced Sensitivity to Growth Inhibition by S-Fluazifop Acid DNA sequences encoding the 2-arylpropionyl-CoA epimerase protein sequence AAR49827 in the GENESEQP Derwent database or P70473 (Swissprot) comprised within the DNA sequences of GENESEQN Derwent database accession AAQ44447 or EMBL accession RN2ARYLCO, respectively are obtained either by RT-PCR or synthetically to optimise expression in plant tissues. Flanking PCR-primer or synthetic DNA sequences are designed to place useful unique restriction sites for cloning. Preferably and in the case where the epimerase coding sequence does not contain confounding internal sites, an Nco1 or Nde1 site is placed at the 5' end to facilitate the cloning of in-frame fusions with sequences added 5' to the ORF. Alternatively, where restriction sites are placed upstream of the ATG translational start site intervening sequences are designed to conform to plant translational concensus sequences such as according to Kozak.

DNA sequences encoding the 'long-chain' acyl CoA synthetases protein sequence P18163 or P39518 (Swissprot) comprised within the DNA sequences of EMBL accessions J05439 or X77783, respectively are obtained either by RT-PCR or synthetically. Flanking PCR-primer or synthetic DNA sequences are designed to place useful unique restriction sites for cloning. Preferably and in the case where the epimerase coding sequence does not contain confounding internal sites, an Nco1 or Nde1 site is placed at the 5' end to facilitate the cloning of in-frame fusions with sequences added 5' to the ORF. Alternatively, where restriction sites are placed upstream of the ATG translational start site intervening sequences are designed to conform to plant translational concensus sequences such as according to Kozak.

Similar to Examples 1 and 2, the above coding sequences are cloned initially into pUC19 or into bluescript sk. The coding sequences are then excised with suitable restriction enzymes, preferably using an Nco 1 site at the 5' end of the coding sequence, into pMJB1 to create alternative in-frame fusion expression cassettes, comprising in a 5' to 3' direction, CaMV35S promoter, TMV translational enhancer, acyl CoA synthetase or epimerase coding sequence-nos terminator. pMJB1 is a pUC19-derived plasmid which contains a plant operable double-enhanced CaMV35S promoter; a TMV omega enhancer and a nos terminator sequence. A schematic representation of pMJB1 is depicted in FIG. 2 of WO 98/20144.

In this way a series of pMJB1 derivatives are created, pMJ35S_AAR49827 etc and pMJ35S_P18163 etc comprising alternative epimerase and acyl CoA synthetase expression cassettes, respectively. Using standard techniques these are, optionally, further cloned into vectors such as pUbiHyg which comprise plant selectable marker genes.

Figure 3A:
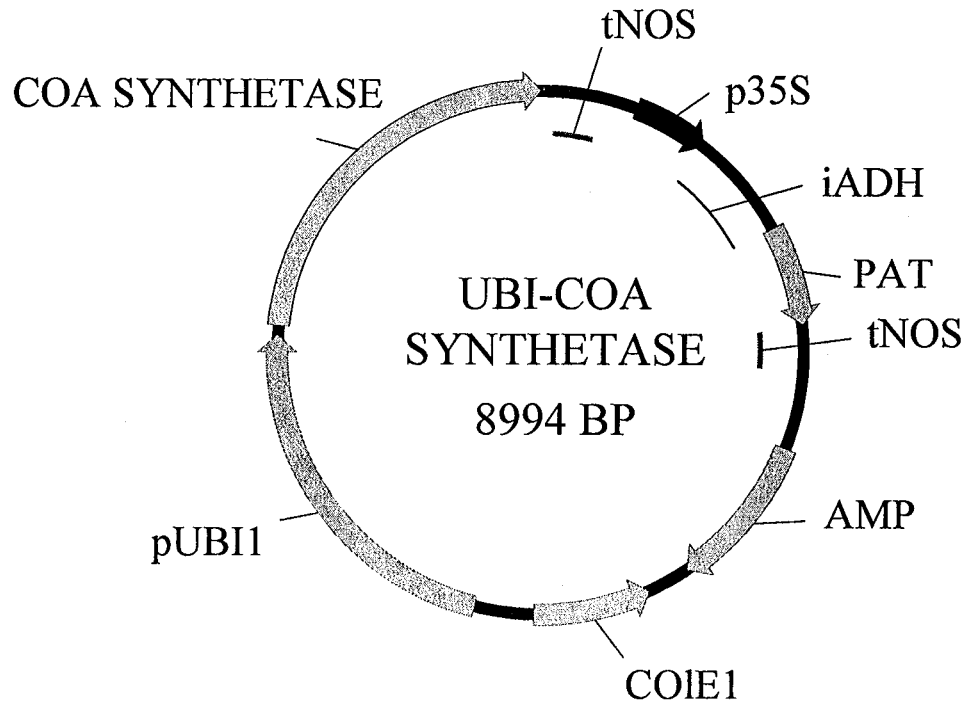
FIG. 3a is a map of the plasmid Ubi-CoA synthetase, wherein PUB11-01-01 has EMBL accession number SM29159 and CoA synthetase has number J05439.
Figure 3B:
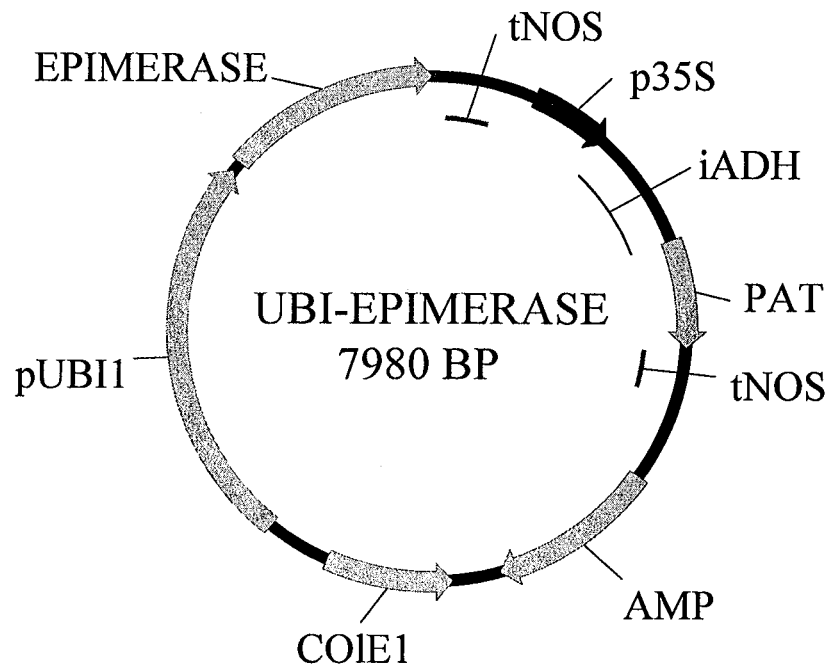
FIG. 3b is a map of the plasmid Ubi-Epimerase, wherein Epimerase has EMBL accession number Y0817Z.

Alternatively, two constructs, one for expression of 'long-chain' acyl CoA synthetases and the other for expression of 2-arylpropionyl-CoA epimerase are built according to the schematic designs of FIG. 3A and FIG. 3B. In 3A, the DNA construct comprises, in the 5' to 3' direction, a maize polyubiquitin promoter region (EMBL: ZM29159), the DNA sequence encoding acyl-CoA synthetase (EMBL: J05439), a nos terminator region, a CMV 35S promoter region, a region encoding a 5' untranslated leader sequence comprising the maize ADH intron, a DNA sequence encoding phosphonothricin acetyl transferase and a nos terminator. As usual, this entire DNA construct is cloned into a suitable site in a vector (e.g a pUC derivative) comprising an E. coli origin of replication and an ampicillin resistance gene. Construct 3B is the same except that the DNA sequence encoding acyl-CoA synthetase is replaced with a DNA sequence encoding 2-arylpropionyl-CoA epimerase (EMBL: Y08172).

These vectors, singly and in combination are transformed into maize plant cell culture using whiskers. For example, cell suspensions of BMS cells are transformed by contacting cells with silicon carbide whiskers coated with DNA using methods essentially as described by Frame et al (1994), Plant J., 6, 941-948. Transformed callus so generated is selected on the basis of differential growth in medium containing a range of concentrations of selecting agent which, depending on the DNA used for transformation might, for example, be glyphosate, hygromycin, L-phosphinothricin or kanamycin. In the case of the constructs depicted in FIGS. 3A and 3B, the selection is carried out on DL phosphinothricin or a derivative thereof. Stably transformed lines are selected as callus which is propagated and continues to grow in selection agent.

For example, following transformation using silicon carbide whiskers, the BMS cells are grown on MS media supplemented with 1 mg/L Bialaphos. After 2 weeks the cells are transferred to MS based media supplemented with 5 mg/L Bialaphos, where they stay for the 6-8 weeks. Resistant calli are formed are transferred to MS media supplemented with 2 mg/L Bialaphos. Stably transformed calli are transferred into a liquid MS based media where they were allowed to grow for 2 weeks. After this period the cells are pelleted and re-suspended into a 1:10 dilution of medium. They are then distributed evenly into a 6 well assay plate and exposed to 2.5 ppm and 10 ppm of the R or S fluazifop. After 4 days in the presence of either R or S fluazifop, 0.1 ml of the settled volume of cells is removed from the wells, washed with fresh liquid MS media and plated onto solid MS based media. The ability of the cells to actively grow and divide was scored after 7 days.

The transformed lines are compared with untransformed lines in respect of sensitivity to S-fluazifop, S-fluazifop butyl or similar S-aryloxyphenoxypropionates and derivatives. DNA coding sequences encoding enzymes preferable for use in the method of the invention are selected as those sequences which, when expressed in BMS cells, encode an enzyme or combination of enzymes transform the phenotype of the transformed maize cells from only being sensitive to growth inhibition by relatively high concentrations of S fluazifop or S-fluazifop butyl to being sensitive to much (at least 2-3 fold) lower concentrations.

DNA coding sequences so selected are then used, as described in the other examples, to create wheat plant lines which are either male or female sterile dependent upon exogenous application of S-fluazifop or S-fluazifop esters.

EXAMPLE 12

Site-Directed Mutagenesis to Generate Genes Encoding D-Amino Acid Oxidases which Oxidise D-Phosphinothricin This example concerns the production of genes which encode variants of R. gracilis D-amino oxidase having improved ability to oxidise D-phosphinothricin. These genes are used in preferred embodiments of the invention, described in the other examples, where sterility is made conditional upon application of D-phosphinothricin. In the current example these genes encode enzymes having a single amino acid change at position '213' and/or at position '238'. The methionine at the '213' position is identified as the M in the native protein sequence motif RCTMDSS (SEQ ID #10). The tyrosine at position 238 is identified as the 'Y' within the native protein sequence motif GGTYGVG (SEQ ID #11). There are many approaches known in the art to providing a series of genes encoding a series of D-amino acid oxidase variants with amino acid changes at one or both of these positions. The choice of DNA template for mutagenesis also depends upon the use. Thus, for example, where the intended use of the mutant gene is for expression in plants then a synthetic DNA which encodes an R. gracilis D amino acid oxidase such as SEQ ID#7 is a suitable starting point. On the other hand, where the intended immediate use of the mutant gene is to use as a starting point for further rounds of mutagenesis and improvement in a yeast-based selection system (as in Example 13) then the native DNA sequence (optionally improved for expression in S. cerevisiae) is more suitable.

A preferred method for providing suitable variants of R. gracilis D amino acid oxidase is through the use of degenerate oligonucleotides using Strategenes Quickchange mutagenesis kit. Methods used are according to the manufacturers instructions.

For example (in the case that the native R. gracilis DNA sequence encoding D-amino acid oxidase be the template DNA for mutagenesis) pairs of 'top' (RGMUTTOP) and 'bottom' (RGMUTBOT) degenerate oligonucleotides may suitably be of 50-250 nucleotides in length and designed to comprise, within them, sequence regions as follows. RGMUTTOP comprises within it a sequence (SEQ ID #8)

```
tccccatgcaagcgatgcacgNNNgactcgtccgacccgcttctcccgc ctacatcattccccgaccaggtggcgaagtcatctgcggcgggacgNNNg gcgtgggagactgggacttg.
```

RGMUTBOT comprises within it a sequence (SEQ ID #9)

```
caagtcccagtctcccacgccNNNcgtcccgccgcagatgacttcgccac ctggtcggggaatgatgtaggcgggagaagcggggtcggacgagtcNNNc gtgcatcgcttgcatgggga
```

In addition, these two oligonucleotides, RGMUTTOP and RGMUTBOT comprise at each end, sequences which, once the two oligonucleotides are annealed with each other will constitute 5' and 3' ends which will exactly match the ends created when the template DNA is cut at a suitable pair of unique restriction sites (i.e designed so that the annealed oligonucleotides can replace a unique restriction fragment cut out of the D-amino acid oxidase encoding template DNA).

0.5 to 1.0 ug of each oligonucleotide is transferred to a 0.5 ml Eppendorf centrifuge tube and heated at a suitable temperature (e.g 94 C, depending on calculated melting points) for 5 minutes and annealed slowly by cooling to room temperature. Template DNA (for example pYES6/CT yeast shuttle vector) is then cut with two restriction enzymes (according to the two unique restriction sites in the template DNA which span the region including the two codons to be replaced and that characterise the ends of the annealed DNA), gel purified, ligated with the annealed oligonucleotide, and transformed into yeast as, for example, described in example 13, so that the alternative D-amino acid oxidases created by mutagenesis are expressed in yeast. Then, as described, yeast clones which yield the best growth on analogues of D phosphinothricin (such as D-homocysteic acid) or on D-phosphinothricin (when the PAT gene is co-expressed) as sole nitrogen source are selected as those containing the variant D-amino acid oxidase encoding sequences with the desired properties. Alternatively D-amino acid oxidase expression is carried out in some microorganism other than yeast and, for example, under expression control of the t7 promoter of a pET vector in an E. coli lysogen. In this case, following transformation, individual colonies may be picked, replica plated, grown, induced, lysed and screened for the desired substrate activity versus D phosphinothricin using methods known in the art (for example, a fluorimetric screen for peroxide generation or a colorimetric assay for ammonia generation). The yeast or other microbial clones thus selected are grown up, DNA is prepared and the full length D-amino acid oxidase DNA sequence cloned via proof reading PCR and cloning into pCRBlunt II using Invitrogens Zero Blunt TOPO kit. The D-amino acid oxidase encoding sequences characterising the selected clones are determined. These D-amino acid oxidase coding sequences are further subcloned for expression in a pET vector (e.g Novagen pET 24a) and transformed into E. coli BL21 DE3. The cells are grown in a fermenter on LCM50 medium containing 100 ug/ml kanamycin, induced with IPTG, harvested, broken and the extract part-purified and assayed for D-amino acid oxidase activity (as detailed below). D-amino acid oxidase genes are selected which encode D-amino acid oxidase enzymes yielding acceptable stability and the highest activity (kcat/Km) per mg of pure protein versus D-phosphinothricin at pH 7.0.

Additionally a series of particular DNA sequences encoding particularly targeted D-amino acid oxidase enzymes are generated. In particular, genes encoding Rhodotorula gracilis D amino acid oxidase with an arginine, serine, cysteine, lysine, asparagine or alanine replacing the methionine at position 213 and/or a histidine, serine, cysteine, asparagine or alanine replacing the tyrosine at position 238. The methods used are the same as described above except that, rather than a mixture of oligonucleotides, individual oligonucleotide pairs are designed and used to effect each single or double amino acid change. Each resulting mutant D-amino acid oxidase coding sequence is cloned for (untagged) expression behind the T7 promoter in Novagen pET 24A and transformed into E. coli BL21 DE3. The cells are grown in a 1.0 l fermenter in LCM50 medium supplemented with 100 ug/ml kanamycin, induced for expression with 1 mM IPTG and harvested by low-speed centrifugation.

LCM50 Medium Contains (in 1 Liter)

$KH_2PO_4$ (3 g), $Na_2HPO_4$ (6 g), NaCl (0.5 g), Casein hydrolysate (Oxoid) (2 g), $(NH_4)_2SO_4$ (10 g), Yeast Extract (Difco) (10 g), Glycerol (35 g) (these ingredients are made up in solution and autoclaved). The following additional ingredients are filter sterilised as solutions and added to the media: $MgSO_4$ (2.5 ml of 246.5 mg/ml solution), Thiamine.HCl (1 ml of of 8 mg/ml soln.) $CaCl_2.2H_2O$ (0.2 ml of 147 g/l solution), *Fe $SO_4.7H_2O$/Citric acid stock (2 ml), **Trace element solution (5 ml) and make up to 1 liter.

*Fe $SO_4.7H_2O$/Citric acid stock per 100 ml consists of Fe $SO_4.7H_2O$ (0.415 mg), Citric acid (0.202 mg).

** The Trace element solution composition per 1 ml is $AlCl_3.6H_2O$ (20 mg), $CoCl_2.6H_2O$ (8 mg), $KCo(SO_4)_2.12H_2O$ (2 mg), $CuCl_2.H_2O$ (2 mg), $H_3BO_3$ (1 mg), KI (20 mg), $MnSO_4.H_2O$ (0.8 mg), $Na_2MoO_4.2H_2O$ (4 mg), $ZnSO_4.7H_2O$ (4 mg)

Approximately 7 g wet weight of cells is washed in water. The cells are resuspended in an equal volume of 50 mM/Mops/KOH buffer at pH 7.0 containing 2 mM EDTA, 2 mM DTT and 0.01 mM FAD. Cells are evenly suspended using a glass homogeniser and then disrupted using a one shot head in the Constant Systems (BudBrooke Rd, Warwick U.K.) Basic Z cell disrupter at 13500 psi. The crude extract is kept cold (~4° C.) centrifuged at 30,000 gav for 1 h and the pellet discarded. Some of the extract protein is run out on an SDS PAGE gel stained with Coomassie Blue and, through side by side comparison with similarly prepared extracts of cells containing only 'empty' pET vector it is estimated that 2-50% of the total soluble protein in the extract is D-amino acid oxidase. Some of the extract protein is exchanged into 50 mM Mops/KOH buffer at pH 7.0 containing 0.01 mM FAD. This is diluted with the same buffer in a standard oxygen electrode cell (calibrated at 25° C. between zero and a saturated concentration of oxygen). Optionally, the D-amino acid oxiadse is further purified using ion-exchange, phenyl sepharose, fractional ammonium sulphate precipitation and gel filtration. Assays, at 25° C., are started by addition of a 200 mM solution of the ammonium salt of DL phosphinothricin to the diluted enzyme. The final reaction volume in the oxygen electrode cell is 2 ml. Rates of oxygen consumption (after subtraction of any drift in the bases line) are measured. The M213R (arginine replacement for methionine) mutant form of *R. gracilis* D amino acid oxidises DL phosphinothricin at a rate of ~14 nmol/min/mg of protein of crude extract (the estimated purity of the D-amino acid oxidase in the extract being 35+/−15% of the total protein). The M213S (serine replacement for methionine) mutant form of *R. gracilis* D amino acid oxidises DL phosphinothricin at a rate of ~4 nmol/min/mg of protein of crude extract (the estimated purity of the D-amino acid oxidase in each extract being 35+/−15% of the total protein). In control experiments the pure L-form is not oxidised at all and, depending on concentration, the pure D form is oxidised at up to twice the rate that the DL is. Under similar conditions, the native (unmutated) *R. gracilis* D-amino acid oxidase exhibits no significant (<0.4 nmol/min/mg) ability to oxidise DL or D-phosphinothricin.

EXAMPLE 13

Mutation and Selection to Generate D-Amino Acid Oxidase Genes Encoding Enzymes with Improved Specificity (kcat/Km) for the Oxidation of D-Phosphinothricin The native *Rhodotorula gracillis* D-amino acid oxidase coding sequence is cloned into Invitrogen's pYES6/CT shuttle vector as a HindIII/PmeI fragment downstream of the GAL1 promoter. Similarly the native *Rhodotorula* D-amino acid oxidase coding sequence is cloned into the pAUR123 protein expression shuttle vector (Panvera) as an XbaI fragment downstream of the ADHI constitutive promoter. Construction of these vectors is performed in *E. coli* followed by transformation into S288C *Saccharomyces cerevisiae*. Where appropriate, the PAT gene is used to replace the blasticidin or aureobasidin antibiotic resistance genes on the pYES6/CT/ pAUR123 vectors respectively and DL phosphinothricin rather than antibiotic used to maintain selection. In addition, sequences encoding the M213R or M213S gene or M213S, Y238S mutant forms of *Rhodotorula* D-amino acid oxidase are cloned in place of the wild-type coding sequence.

Further mutant variants of D-amino acid oxidase are created using various methods of mutagenesis. For example, multiple variants of the D-amino acid oxidase coding sequence are generated by Mn2+-poisoned PCR, the mixed population is cloned in front of the GAL1 or ADH1 promoters of the two shuttle vectors, transformed into yeast and selection made based upon the ability of the new sequence to confer upon yeast the ability to grow on D-homocysteic acid as sole nitrogen source. Alternatively mutation and selection is carried out directly on the transformed yeast. For example, yeast transformed with the above plasmids are grown up in a fermenter in the presence of a chemical mutagen such as EMS in a nitrogen-limited culture medium which contains 10-50 mM D-homocysteic acid or (in the case that the PAT gene is expressed) 20-100 mM DL phosphinothricin and induced for D-amino acid oxidase expression (e.g grown on galactose as carbon source). After successive subculturings, subcultures growing on the D-homocysteic acid or phosphinothricin as sole N source are identified, plated out and the D-amino acid oxidase coding sequences subcloned, sequenced and expressed in *E. coli* for further characterisation.

In a further, preferred, method mutagenesis is carried out on the two shuttle vectors by using amplification and passage through *E. coli* strain XL1-red. This strain is deficient in three primary DNA repair pathways, mut S, mut D and mut T. This results in a 5000 fold increase in mutation rates during DNA replication. The protocol used is according to Stratagene. For example, 10 ng of shuttle vector is transformed into *E. coli* strain XL1-red, cells are grown up and then plated out onto L-Broth agar containing ampicillin for 24 h. From each plate >200 transformant lots of colonies are pooled by scraping the colonies off the plate into L broth and then 1 in 100 and 1 in 1000 dilutions are grown and successively subcultured in L-broth/ampicillin at 37° C. for 1-2 weeks so that a large number of cell-divisions have ensued. A similar procedure is carried out starting from a number of plates. Minipreps of shuttle vector DNA are prepared from cells grown overnight and transformed back into yeast. The transformed yeast are grown up and colonies containing improved D-amino acid oxidases selected as described above.

Alternatively, D-amino acid oxidase expression and selection is carried out in some microorganism other than yeast and, for example, under expression control of the t7 promoter of a pET vector in an *E. coli* lysogen. In this case, the D-amino acid oxidase coding sequence (optionally mutagenised by Mn2+-poisoned PCR) is cloned into a pET vector, transformed into *E. coli* XL1red and after passage for a number of generations, transformed back into an *E. coli* lysogen such as *E. coli* BL212 DE3. Individual colonies may then be picked, replica plated, grown, induced with IPTG, lysed and screened for the desired substrate activity versus D phosphinothricin using methods known in the art (for example, a fluorimetric screen for peroxide generation or a colorimetric assay for ammonia generation).

Alternatively, mutagenesis and selection for improved D-amino acid oxidase coding sequences is carried out directly in *Rhodotorula gracilis*. *R. gracilis* are grown in minimal medium with D-alanine or D-glutamate as sole nitrogen source, subjected to successive rounds of mutagenesis with EMS and selection via subculturing into media of increasing stringency where, the sole nitrogen source is shifted from D-glutamate towards D-homocysteic acid. In a variant of this example the *Rhodotorula gracilis* is transformed with one of the yeast vectors described above so that it expresses PAT (either when grown on galactose or constitutively) and the final stage of stringent selection is made on DL phosphinothricin or D phosphinothricin as sole nitrogen source.

Optionally the media used for selection of yeast contain a low concentration of solvent (e.g 0.1% DMSO).

EXAMPLE 14

Production of D-Phosphinothricin in an Enantiomerically Pure Form

*E. coli* BL21 DE3 codon plus RIL is transformed with Novagen pET 24A having the PAT coding sequence (A02774) cloned for (untagged) expression behind the T7 promoter. These cells are grown to a density of ~40 $OD_{600\,nm}$ in a 10 liter fermentor of LCM 50 medium containing kanamycin, induced with 0.2 mM IPTG, harvested by low speed centrifugation and quickly transferred into minimal media containing 9.91 g of the ammonium salt of D/L phosphinothricin (PPT).

Minimal Media (in 1 Liter) is.

$Na_2HPO_4$ (6 g), $KH_2PO_4$ (3 g), NaCl (1 g), $NH_4Cl$ (1 g) were dissolved in water and autoclaved and the following solutions were added after filter sterilisation:

$CaCl_2$ (1 ml of 14.7 g/l), $MgSO_4$ (1 ml of 246.5 g/l), Thiamine.HCl (5 ml of 1 mg/ml)

Glucose (30 ml of 20% solution autoclaved separately), DMSO 0.5 ml.

Fermentation details are as follows. A 10 liter fermenter of LCM 50 medium is inoculated with an LB broth-grown inoculum (200 ml) of *E. coli* BL21 DE3 codon plus RIL containing the PAT gene and is maintained at 30° C., 200 rpm stirring rate, pH6.5, oxygen concentration 50% air-saturated. After ~12 h the culture grows to an $OD_{600\,nm}$ of ~30. The culture is then induced for PAT expression by the addition of 0.2 mM IPTG. After 1.5 h, the culture typically grows further to an $OD_{600\,nm}$ of ~40, before the cells are harvested by centrifugation and washed in 8 liters of minimal medium. The cells are spun once again and resuspended to a final volume of 10 liters in the fermenter in minimal media containing 9.91 g of the commercially available ammonium salt of D/L-phosphinothricin and a further 0.2 mM IPTG. The temperature is increased to 37° C. and samples of the fermenter medium monitored by proton and phosphorous NMR in order to determine a) when the glucose levels have dropped substantially and need replenishing and b) the extent of conversion of phosphinothricin to n-acetyl phosphinothricin. Over the course of ~12 h, ~500 g of glucose are added to the fermenter. The formation of n-acetyl phosphinothricin is observed to start after a few hours and by ~20 h reaches >93% conversion of the L-PPT (46.5% v of the D/L) to N-acetyl-L-PP. The fermentation medium is harvested soon thereafter with the cells being remove by low-speed centrifugation.

D-PPT is purified from the fermentation medium using ion-exchange chromatography. The fermentation medium (~9.5 l) is stored at 4° C. It is mixed with 900 ml of Dowex 50W-X8 200-400 mesh cation exchange resin (pre-prepared with HCl) in the $H^+$ form such that the pH of the supernatant above the resin drops to ~pH 3.0. The Dowex resin is allowed to settle out under gravity and the supernatant together with a 2l water rinse of the Dowex resin is decanted off and then centrifuged to clarify. The washed Dowex is discarded (to eventually be recycled). The clarified supernatant is then extracted via a separating funnel with ethyl acetate (¼ of the volume of supernatant) and the aqueous fraction (~12 l) retained. A further 2.3 l of $H^+$ form Dowex 50W-X8 resin is then added and stirred with the ~12l. The resin is then allowed to settle out. The pH of the supernatant above the resin is ~pH 1.6 at this stage. The supernatant is decanted off and discarded and the resin washed with ~12 liters of water and, again, allowed to settle out. Again, the supernatant is discarded and the resin is poured onto a sintered Buchner funnel filter and rinsed with a further ~4.5 l of water (to remove most of the residual N-acetyl-phosphinothricin). The major D-phosphinothricin-containing fraction is eluted from the resin with 15 l of 0.4M ammonium hydroxide, followed by a 1.4 l water rinse of the resin. The pH of this D-phosphinothricin-containing fraction is ~11.4. Optionally, this is reduced to ~pH 10 by the addition of, for example, ~0.13 Moles of acetic acid and ~600 ml of cation exchanger resin in the $H^+$ form. If added, the resin is allowed to settle out. The D-phosphinothricin (supernatant) fraction is then loaded on to a 565 ml (5×28 cm) column of Dowex 1×8-400 mesh anion exchange resin in the OH— form (preequilibrated with NaOH and washed with water). A 0M-0.32M ammonium acetate gradient is applied to the column over 17 column bed volumes. 55 ml fractions are collected throughout. The fractions are monitored by UV at 215 nm and also by proton and 31P NMR. This analysis indicates that highly pure phosphinothricin is eluted between fractions 39 and 78. N-acetyl phosphinothricin is eluted as unbound material and early in the gradient and some glutamate elutes later in fractions 79-90.

Fractions 63 to 78 (corresponding to 6-7.6 bed volumes) constitute the bulk of highly pure phosphinothricin. The phosphinothricin fractions are freeze dried and found to be pure by proton and phosphorous NMR (no other peaks visible apart from acetate, >95% of the organic material is phosphinothricin), although, based upon discrepancies between calculated and observed dry weights it is found that, typically, some residue of inorganic salts (for example ammonium chloride) remain in the phosphinothricin samples. For practical purposes, when the D-phosphinothricin is used (for example to spray on plants) the inorganics can be taken to be inert and only need to be taken account to adjust calculated concentrations when D-phosphinothricin solutions are made of from weighed dry samples.

It is expected that the phosphinothricin isolated according to the above method should be substantially enantiomerically pure D-phosphinothricin. This is verified according to the fluorescent HPLC analysis method of Hori et al. (2002) J. Chrom. B 776, 191-198. For example, 50 ul of either commercial DL phosphinothricin (0.01-10 ug/ml) or of sample is dissolved in 0.1M Borate buffer pH8.5 and mixed with 200 ul of the same Borate buffer. 50 ul of 18 mM FLEC ((+)-1-(9-fluorenyl)ethyl chloroformate) is then added and the mixtures further incubated for 30 mins at 40° C. Excess FLEC is removed by shaking for 3 mins with 500 ul of ethyl acetate. 100 ul of the bottom aqueous layer is removed for HPLC analysis.

An Inertsil ODS2 (15×4.6) 5 uM partical HPLC column is equilibrated with 77% 10 mM aqueous ammonium acetate (pH5.0): 23% Acetonitrile at a flow rate of 0.8 ml/min. A 2 ul sample is injected onto the column and run isocratically over 60 mins and is monitored using fluorescence detection with excitation at 260 nm and emission wavelength at 305 nm. It is observed that the D & L isomers of phosphinothricin are clearly separated and elute at 12.4 and 13.4 mins respectively. A sample of the D phosphinothricin isolated according to the current method is run and is estimated to be at a better than 99% enantiomeric excess. This is estimated on the basis of spiking with known quantities of commercial DL phosphinothricin and observing how small an increase in the right-hand, 13.4 minute peak is detectable against the background of the apparently single, 12.4 min peak yielded by the sample.

In addition, the HPLC method is used to estimate the amount of phosphinothricin on the basis of peak integration and comparison with a standard curve. Additionally total amounts of phosphinothricin are estimated by integration of NMR signals It is estimated that, in total, from the starting ~9.91 g of DL racemate, ~1.9 g (38% yield) of pure D phosphinothricin ammonium salt in an enantiomeric excess of >99% is produced. 50-70% of the dry weight of the sample comprises inorganic salts which are carried through. Optionally these are removed by further steps of ion exchange and freeze drying (following exchange to volatile salts).

EXAMPLE 15

Production of Enantiomerically Pure S-Fluazifop and S-fluazifop Butyl

S-Fluazifop acid and its esters are produced using methods, analogous to those well-known for R-Fluazifop, and as described in the literature (for example D. Cartwright, in Proceedings of the Brighton Crop Protection Conference—Weeds (1989) 2, 707-716 and references therein). Similarly, methods for producing the RS racemate are well known. Optionally, pure S-Fluazifop is produced via preparative chromatographic resolution from the RS racemate (for example as described by Bewick (1986) in Pesticide Sci., 17, 349-356). From an RS mixture of fluazifop butyl, the S enantiomer is isolated in an enantiomeric excess better than 97% using the HPLC method described by Bewick. Alternatively, S Fluazifop is directly resolved from the RS mixture of acids by chromatography down a suitable cyclodextrin column (Journal of Chromatography (1993), 634(2), 197-204.) or by using other column chromatographic methods (Biomedical Chromatography (1998), 12(6), 309-316; Journal of Chromatography, A (2001), 937(1-2), 135-138). A further method of general preparative utility for isolating enantiomerically pure S aryloxyphenoxypropionic acids and their esters is described in Chimiques Des Pays-Bas (1991) 110 (05), 185-188. In this case a carboxylesterase NP enzyme is produced and used for enantio-selective hydrolysis of racemic esters of aryloxyphenoxypropionates (the resulting acids being readily separable from the remaining ester).

In a preferred method, enantiomerically pure S-Fluazifop is produced by a direct synthetic method. In the first step the intermediate 4-(5-trifluoromethyl-oyridin-2-yloxy)-phenol is synthesised.

Preparation of 4-(5-trifluoromethyl-oyridin-2-yloxy)-phenol

To a suspension of potassium carbonate (13.81 g, 99 mmol) in dry DMF (200 mls), at room temperature is added hydroquinone (10.0 g, 91 mmol) and the mixture is stirred for 30 mins. 2-Chloro-5-trifluoromethylpyridine (16.49 g, 91 mmol) is added and the mixture warmed to 90° C. for 16 hours. The reaction mixture is poured into water, acidified with dilute HCl and then extracted with ethyl acetate. The combined organic layers are washed with water, dried over magnesium sulphate, filtered and the solvent removed under reduced pressure. Column chromatography on silica gel using 10-20% ethyl acetate/hexane as eluent yields, for example, ~10.22 g of 4-(5-trifluoromethyl-oyridin-2-yloxy)-phenol in ~44% yield.

$\delta$H (400 MHz; CDCl$_3$) 8.45, s, 1H; 7.9, dd, 1H; 7.0, m, 1H; 7.0, d, 2H, 6.8, d, 2H, 5.75, s, 1H.

In a further step the intermediate (R)-2-hydroxypropionic acid benzylester is synthesised.

Preparation of (R)-2-hydroxypropionic acid benzylester

To a suspension of sodium D-lactate in DMF at 0° C. under nitrogen benzyl bromide is added dropwise. The mixture is stirred at 0° C. for 16 hours. The solvent is then removed under reduced pressure, and the residue partitioned between diethyl ether and water. The layers are separated, and the organic phase is washed with saturated sodium bicarbonate, brine, then dried over magnesium sulphate, filtered and the solvent removed under reduced pressure to give (R)-2-hydroxypropionic acid benzylester as a colourless oil. For example 2.81 g are made in 88% yield.

$\delta$H (400 MHz; CDCl$_3$) 7.4, m, 5H, 5.23, s, 2H, 4.35, q, 1H; 2.85, d, 1H, 1.45, d, 3H.

In a further step the intermediate (S)-2-[4-(5-Trifluoromethyl-pyridin-2-yloxy)-phenoxy]-propionic acid benzyl ester is synthesised.

Preparation of (S)-2-[4-(5-Trifluoromethyl-pyridin-2-yloxy)-phenoxy]-propionic acid benzyl ester To a solution of 4-(5-trifluoromethyl-pyridin-2-yloxy)-phenol (2.90 g, 11.4 mmol) and (R)-2-hydroxypropionic acid benzyl ester (2.25 g, 12.5 mmol) in dry THF (100 mls) at 0° C. under nitrogen is added triphenylphosphine followed by dropwise addition of diisopropylazodicarboxylate (3.36 mls, 17 mmol). The resulting yellow mixture is stirred for 1 hr then left the stand for 16 hours. The reaction mixture is partitioned between water and ethyl acetate and the layers separated. The aqueous is further extracted with ethyl acetate and the combined organic layers dried over magnesium sulphate, filtered and the solvent removed under reduced pressure. Column chromatography on silica gel using 10% ethyl acetate/hexane as eluent yielded (S)-2-[4-(5-Trifluoromethyl-pyridin-2-yloxy)-phenoxy]-propionic acid benzyl ester as a colourless oil. In one example 3.25 g are made representing 69% yield and in >99% ee (as determined by nmr).

$\delta$H (400 MHz; CDCl$_3$) 8.42, s, 1H, 7.89, dd, 1H, 7.35, m, 5H, 7.25, d, 2H, 6.95, d, 1H, 6.9, d, 2H, 5.22, s, 2H, 4.78, q, 1H, 1.65, d, 3H.

In a final step the S acid is made.

Preparation of (S)-2-[4-(5-trifluoromethyl-pyridin-s-yloxy)phenoxy]-propionic acid A mixture of (S)-2-[4-(5-Trifluoromethyl-pyridin-2-yloxy)-phenoxy]-propionic acid benzylester (3.12 g) and Pd/C (5%, 0.1 g) in ethyl acetate (20 mls) is stirred under a hydrogen atmosphere at 2.5 bar for 2.5 hours. The reaction mixture is filtered through celite, and the solvent removed under reduced pressure. Column chromatography on silica gel using 25% ethyl acetate/hexane 1% acetic acid as eluent gave (S)-2-[4-[5-trifluoromethyl-pyridin-s-yloxy)phenoxy]-propionic acid as a colourless oil. For example, 2.41 g is made in 99% yield at 99% ee+/−0.5% (as determined by nmr).

DH (400 MHz; CDCl$_3$) 8.42, s, 1H, 7.9, dd, 1H, 7.1, m, 2H, 6.9, m, 3H, 4.8, q, 1H, 1.7, d, 3H.

Similar methods to those above are used to produce S-enantiomers of other aryloxyphenoxypropionate herbicides (for example, fenoxaprop, haloxyfop, fluozifop and quizalofop and their esters).

The skilled man will appreciate that, while illustrative of the invention, the above examples do not limit its scope.

The invention claimed is:

1. A method of using D-phosphinothricin as a hybridization agent to produce dicotyledon hybrid seed, comprising the steps of:
   a. providing conditionally female sterile transgenic plants comprising a transgene, expressed by a tissue specific female floral promoter, said transgene encoding a mutant D-amino acid oxidase derived from *Rhodotorula gracilis*, said oxidase comprising a lysine at position 58 rather than a phenylalanine in the wild type sequence,
   b. applying exogenously to the conditionally female sterile transgenic plants an amount of D-phosphinothricin at an appropriate time;
   c. selecting for the conditionally female sterile transgenic plants which produce little or no seed after application of D-phosphinothricin and which produce at least near normal levels of viable pollen;
   d. pollinating a female fertile plant with the pollen of step (c); and
   e. harvesting dicotyledon hybrid seed from the plant of step (d).

2. The method of claim 1, wherein the tissue specific female floral promoter is selected from the group consisting of delta S13 and Stig1.

3. The method of claim 1, wherein the mutant D-amino acid oxidase is derived from a *Rhodotorula gracilis* sequence set forth in SEQ ID NO: 7.

4. The method of claim 1, wherein the transgene encoding an oxidase is optionally operably linked to an upstream sequence encoding a chloroplast transit peptide.

5. The method of claim 1, wherein the conditionally female sterile plants are tobacco plants.

6. The method of claim 1, wherein the amount of D-phosphinothricin is between 0.25 kg/ha and 20 kg/ka.

7. The method of claim 1, wherein the D-phosphinothricin is exogenously applied by a technique selected from the group consisting of foliar spray and root drench.

8. The method of claim 7, wherein the D-phosphinothricin is exogenously applied by root drench and further applied by flooding a D-phosphinothricin solution directly into buds of emerging florets of the conditionally female sterile plants.

9. The method of claim 8, wherein the D-phosphinothricin solution is from 10 mM to 200 mM.

10. The method of claim 1, wherein the appropriate time is selected from the group consisting of prior to flowering and during the early stages of flowering.

11. The method of claim 1, wherein the D-phosphinothricin is comprised in a racemic mixture of D- and L-phosphinothricin.

12. The method of claim 1, wherein the conditionally female sterile transgenic plants are tolerant to L-phosphinothricin.

13. A method of using D-phosphinothricin as a hybridization agent to produce dicotyledon hybrid seed, comprising the steps of:
   a. providing conditionally male sterile transgenic plants comprising a transgene expressed by a tissue specific male floral promoter, said transgene encoding a mutant D-amino acid oxidase derived from *Rhodotorula gracilis*, said oxidase comprising a lysine at position 58 rather than a phenylalanine in the wild type sequence;
   b. applying exogenously to the conditionally male sterile transgenic plants an amount of D-phosphinothricin at an appropriate time;
   c. selecting for the conditionally male sterile transgenic plants which produce little or no pollen after application of D-phosphinothricin;
   d. pollinating the product of step (c) with the pollen of a male fertile plant; and
   e. harvesting dicotyledon hybrid seed from the plant of step (d).

14. The method of claim 13, wherein the tissue specific male floral promoter is selected from the group consisting of TA29 and a fragment of TA29.

15. The method of claim 14, wherein the fragment of TA29 is optionally operably linked to an upstream CaMv promoter sequence fragment.

16. The method of claim 13, wherein the mutant D-amino acid oxidase is derived from a *Rhodotorula gracilis* sequence set forth in SEQ ID NO: 7.

17. The method of claim 13, wherein the conditionally male sterile plants are tobacco plants.

18. The method of claim 13, wherein the amount of D-phosphinothricin is between 0.25 kg/ha and 20 kg/ka.

19. The method of claim 13, wherein the D-phosphinothricin is exogenously applied by a technique selected from the group consisting of foliar spray and root drench.

20. The method of claim 19, wherein the D-phosphinothricin is exogenously applied by root drench and further applied by flooding a D-phosphinothricin solution directly into buds of emerging florets of the conditionally male sterile plants.

21. The method of claim 20, wherein the D-phosphinothricin solution is from 10 mM to 200 mM.

22. The method of claim 13, wherein the appropriate time is selected from the group consisting of prior to flowering and during the early stages of flowering.

23. The method of claim 13, wherein the D-phosphinothricin is comprised in a racemic mixture of D- and L-phosphinothricin.

24. The method of claim 13, wherein the conditionally male sterile transgenic plants are tolerant to L-phosphinothricin.

* * * * *

SEQUENCE LISTING

<160> NUMBER OF SEQ ID NOS: 11

<210> SEQ ID NO 1
<211> LENGTH: 831
<212> TYPE: DNA
<213> ORGANISM: Synechocystis sp.

<400> SEQUENCE: 1

```
atggaacgat tagaacacca cgccagcttt gggggttggc aaagcgttta tagccatcac      60
agcgctgtgc ttaattgcac catgaacgtt ggcgtttacc tgcctcccca ggctactaac     120
caacattgcc cagttttgta ctggctgtct ggcctcacct gtactgaaca aaatgccatc     180
actaaatcgg tctacagca gcacgcagca aagcatggac taattatggt gacgccagac     240
actagccccc ggggtgaagg cgtaactgat tctgaagatt atgacctcgg tatgggagcc     300
ggtttctatc tcaacgccac ccaacctccc tgggcagccc actatcaaat gcatgattac     360
attgtgcaag agctgcctac gtggattgag ctaattttg ccgccaccga tgcccggagt      420
atttttggcc attccatggg gggccatggg gccctagtca ttgccctgcg taatcccggt     480
cgttatcgca gtgtttccac cttctctccc attgttgccc ccactcaagt tccctgggga     540
caaaaggcct tccaagctta tttaggggat aaccagttaa gctggcaagc ttgggatacc     600
tgtgctctga ttaaatcggc tccagagcgg ctaccatttt tcgtggacta tggcgacgct     660
gatccattcc tccctaccca attgcggcca gagttactcc aagcggcctg cacggcggct     720
aaccatcccc tcaccctccg tatgcaaccg ggctatgacc atagctatta ctttattgct     780
agtttcatcg gtgatcacat ggattggcat ggagcggcgc tgctaaacta g             831
```

<210> SEQ ID NO 2
<211> LENGTH: 276
<212> TYPE: PRT
<213> ORGANISM: Synechocystis sp.

<400> SEQUENCE: 2

```
Met Glu Arg Leu Glu His His Ala Ser Phe Gly Gly Trp Gln Ser Val
1               5                   10                  15
Tyr Ser His His Ser Ala Val Leu Asn Cys Thr Met Asn Val Gly Val
            20                  25                  30
Tyr Leu Pro Pro Gln Ala Thr Asn Gln His Cys Pro Val Leu Tyr Trp
        35                  40                  45
Leu Ser Gly Leu Thr Cys Thr Glu Gln Asn Ala Ile Thr Lys Ser Gly
    50                  55                  60
Leu Gln Gln His Ala Ala Lys His Gly Leu Ile Met Val Thr Pro Asp
65                  70                  75                  80
Thr Ser Pro Arg Gly Glu Gly Val Thr Asp Ser Glu Asp Tyr Asp Leu
                85                  90                  95
Gly Met Gly Ala Gly Phe Tyr Leu Asn Ala Thr Gln Pro Pro Trp Ala
            100                 105                 110
Ala His Tyr Gln Met His Asp Tyr Ile Val Gln Glu Leu Pro Thr Trp
        115                 120                 125
Ile Glu Ala Asn Phe Ala Ala Thr Asp Ala Arg Ser Ile Phe Gly His
    130                 135                 140
Ser Met Gly Gly His Gly Ala Leu Val Ile Ala Leu Arg Asn Pro Gly
145                 150                 155                 160
Arg Tyr Arg Ser Val Ser Thr Phe Ser Pro Ile Val Ala Pro Thr Gln
                165                 170                 175
Val Pro Trp Gly Gln Lys Ala Phe Gln Ala Tyr Leu Gly Asp Asn Gln
            180                 185                 190
Leu Ser Trp Gln Ala Trp Asp Thr Cys Ala Leu Ile Lys Ser Ala Pro
        195                 200                 205
Glu Arg Leu Pro Phe Phe Val Asp Tyr Gly Asp Ala Asp Pro Phe Leu
    210                 215                 220
```

Pro Thr Gln Leu Arg Pro Glu Leu Leu Gln Ala Ala Cys Thr Ala Ala
225                 230                 235                 240

Asn His Pro Leu Thr Leu Arg Met Gln Pro Gly Tyr Asp His Ser Tyr
            245                 250                 255

Tyr Phe Ile Ala Ser Phe Ile Gly Asp His Met Asp Trp His Gly Ala
        260                 265                 270

Ala Leu Leu Asn
        275

<210> SEQ ID NO 3
<211> LENGTH: 1374
<212> TYPE: DNA
<213> ORGANISM: Neurospora crassa

<400> SEQUENCE: 3

```
ggaaggaatc agtatggttg gccaaccgcc tcttaccggc ctcaaggtcc tggagtttgc      60
cggtctagct ccaggtcagc cctccatctc tcactttttcc tccgacttac acacacagag     120
gctttcggcc gaaacccggc cgatcttgag gtctcactta cacttcac ttacacttca       180
ctctcacttg gaaaaaaaca aaatgtcaca aaactaattc cccgcttggg aacaggtccc      240
ttcgccgggc tcctcctcgc cgacgctggc gcctccgtcc tgcgcatcga ccgcgccgtc      300
tccggccccg tcgcccgcca agttcccgac caactaaccc gccacaaatc ctccttggtg      360
gtcgacctca agtccccctc cggaatcgcc ctcatcaaat ccctcgccgc cgtatcggac      420
gttctcatcg acccttaccg ccccggcgtc ctggagaagc tcgggctggg ccctctgtc      480
ctgtgcagcg acgaatgcaa ccccgcctc atctacgccc gcctgacggg cttccggcga      540
gacggccggt tcgccaccat ggccgggcac gatatcaact acctggctgt gagcggggtg      600
ttgagtctgc tggggaggaa gggcgagaag ccgacgccgc ccatcaacat tctgggagac      660
tttgccggcg gcggagcggt tttgttccag ggcatcctgc ttgcgctggc cgcgagggag      720
aggacgggca agggacaggt ggtggaggcg aatatcgtcg acggagcgag ttacttggct      780
acttttaacc ggtttgcgct caaaacggcc gtggggaacg caccgagggg ggagaacctg      840
ctggatacgg gctgcccctta ctatgatacg tacgagaccg cggatgggaa gtacatagct      900
gtcggggcgt tggagccgca gtttttcaag gagttggtta aagggttggg gttagaggga      960
caagggtggg aggagaggag aggggacaag gagaattggc ccgagctgag gagggtgttg     1020
gagcacaagt tcaagaccaa aacgaggagg gagtgggagg atatctttga cgggactgat     1080
gcgtgctgca cggcggtgtt tgagtacggc gagatggaaa gggagaggga gcggttggag     1140
ggcgatcaga gacccgtggt tacgcttagg gagacgccct gcttggcgct gaggagcgat     1200
gcgaaggatg ctagccatgg gcaagggccg ggcgtcaagg gggaagcgta tgtaggcatt     1260
cccttgaaac ctggaaaggg aggcgaatct gtcgtggaga agtggcttgg ttggaagaag     1320
ggcaaggagt ttgatgtgtt gaatgggagc gctgtcgcta tcaagtccag actg           1374
```

<210> SEQ ID NO 4
<211> LENGTH: 460
<212> TYPE: PRT
<213> ORGANISM: Neurospora crassa

<400> SEQUENCE: 4

Gly Arg Asn Gln Tyr Gly Trp Pro Thr Ala Ser Tyr Arg Pro Gln Gly
1               5                   10                  15

Pro Gly Val Cys Arg Ser Ser Arg Ser Ala Leu His Leu Ser Leu
            20                  25                  30

Phe Leu Arg Leu Thr His Thr Glu Ala Phe Gly Arg Asn Pro Ala Asp
            35                  40                  45

Leu Glu Val Ser Leu Ile His Phe Thr Tyr Thr Ser Leu Ser Leu Gly
 50                  55                  60

Lys Lys Gln Asn Val Thr Lys Leu Ile Pro Arg Leu Gly Thr Gly Pro
 65                  70                  75                  80

Phe Ala Gly Leu Leu Ala Asp Ala Gly Ala Ser Val Leu Arg Ile
            85                  90                  95

Asp Arg Ala Val Ser Gly Pro Val Ala Arg Gln Val Pro Asp Gln Leu
            100                 105                 110

Thr Arg His Lys Ser Ser Leu Val Val Asp Leu Lys Ser Pro Ser Gly
            115                 120                 125

Ile Ala Leu Ile Lys Ser Leu Ala Ala Val Ser Asp Val Leu Ile Asp
            130                 135                 140

Pro Tyr Arg Pro Gly Val Leu Glu Lys Leu Gly Leu Gly Pro Ser Val
145                 150                 155                 160

Leu Cys Ser Asp Glu Cys Asn Pro Arg Leu Ile Tyr Ala Arg Leu Thr
            165                 170                 175

Gly Phe Arg Arg Asp Gly Arg Phe Ala Thr Met Ala Gly His Asp Ile
            180                 185                 190

Asn Tyr Leu Ala Val Ser Gly Val Leu Ser Leu Leu Gly Arg Lys Gly
            195                 200                 205

Glu Lys Pro Thr Pro Pro Ile Asn Ile Leu Gly Asp Phe Ala Gly Gly
            210                 215                 220

Gly Ala Val Leu Phe Gln Gly Ile Leu Leu Ala Leu Ala Ala Arg Glu
225                 230                 235                 240

Arg Thr Gly Lys Gly Gln Val Val Glu Ala Asn Ile Val Asp Gly Ala
            245                 250                 255

Ser Tyr Leu Ala Thr Phe Asn Arg Phe Ala Leu Lys Thr Ala Val Gly
            260                 265                 270

Asn Ala Pro Arg Gly Glu Asn Leu Leu Asp Thr Gly Cys Pro Tyr Tyr
            275                 280                 285

Asp Thr Tyr Glu Thr Ala Asp Gly Lys Tyr Ile Ala Val Gly Ala Leu
            290                 295                 300

Glu Pro Gln Phe Phe Lys Glu Leu Val Lys Gly Leu Gly Leu Glu Gly
305                 310                 315                 320

Gln Gly Trp Glu Glu Arg Arg Gly Asp Lys Glu Asn Trp Pro Glu Leu
            325                 330                 335

Arg Arg Val Leu Glu His Lys Phe Lys Thr Lys Thr Arg Arg Glu Trp
            340                 345                 350

Glu Asp Ile Phe Asp Gly Thr Asp Ala Cys Cys Thr Ala Val Phe Glu
            355                 360                 365

Tyr Gly Glu Met Glu Arg Glu Arg Glu Arg Leu Glu Gly Asp Gln Arg
            370                 375                 380

Pro Val Val Thr Leu Arg Glu Thr Pro Cys Leu Ala Leu Arg Ser Asp
385                 390                 395                 400

Ala Lys Asp Ala Ser His Gly Gln Gly Pro Gly Val Lys Gly Glu Ala
            405                 410                 415

Tyr Val Gly Ile Pro Leu Lys Pro Gly Lys Gly Glu Ser Val Val
            420                 425                 430

Glu Lys Trp Leu Gly Trp Lys Lys Gly Lys Glu Phe Asp Val Leu Asn
            435                 440                 445

Gly Ser Ala Val Ala Ile Lys Ser Arg Leu Ser Gln

```
                 450              455              460

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
aactgcagct ttttggttag cgaatgc                                       27

<210> SEQ ID NO 6
<211> LENGTH: 35
<212> TYPE: DNA
<213> ORGANISM: Artificial Sequence
<220> FEATURE:
<223> OTHER INFORMATION: Primer

<400> SEQUENCE: 6
cagactagtt ttagctaatt tctttaagta aaaac                              35

<210> SEQ ID NO 7
<211> LENGTH: 1107
<212> TYPE: DNA
<213> ORGANISM: Rhodotorula gracilis

<400> SEQUENCE: 7
atgggatccc aaaagagggt tgtggtgctg ggttccggcg tgataggact cagctccgcg   60
cttatacttg cccggaaggg gtactccgtc cacatcctgg cccgggacct cccagaggat   120
gttagctcac agaccttcgc gtccccttgg gctggagcca actggacccc ttttatgacc   180
ctcactgacg gcccgaggca ggcaaagtgg gaggagtcta cattcaagaa gtgggtggaa   240
cttgtgccaa cggggcatgc catgtggttg aagggaacca ggcgtttcgc ccaaaatgag   300
gacggactgc tcggtcactg gtacaaagat atcaccccca attatagacc cttgccctct   360
tccgaatgtc caccaggcgc tattggcgtg acttatgaca cattgtcagt gcacgctcca   420
aagtactgcc aatacctcgc aagggagctc agaagctggg ggcgacatt cgagcgccgc   480 accgttactt ccctcgagca agcttttgat ggggctgacc tcgtcgttaa cgcgacgggg   540
ctgggtgcca agtccatcgc tggcatcgat gaccaggcgg ccgagcctat tcgcggtcaa   600
acggtgctcg tcaagtcgcc ctgcaaaagg tgtactatgg acagctcgga cccggcatca   660
ccggcgtaca tcatcccgcg gccaggaggc gaagtgattt cggcggtac gtacggggtc   720 ggagactggg atctctcggt caacccagag accgtccagc gcatcctcaa acactgcctg   780
cgcctggatc cgactatttc ttcggacggc acaatcgaag gcatcgaggt gctgcggcat   840
aacgtcggac tcagaccggc gaggagggga ggccctcgcg ttgaagccga gaggattgtt   900
cttccacttg acagaacgaa gagcccctc tcactgggcc gtgggagcgc tcgtgcggcc   960
aaggagaagg aggtgacttt ggtgcatgcc tacggtttct ccagcgctgg ctatcaacag   1020
tcttggggcg cagccgaaga cgtcgcacaa ttggtcgatg aggcgtttca gaggtatcat   1080
ggggccgccc gcgagtctaa gctctga                                      1107

<210> SEQ ID NO 8
<211> LENGTH: 120
<212> TYPE: DNA
<213> ORGANISM: Artificial Sequence
<220> FEATURE:
<223> OTHER INFORMATION: Primer
<220> FEATURE:
```

```
<221> NAME/KEY: misc_feature
<222> LOCATION: (22)..(22)
<223> OTHER INFORMATION: Where n=a,t, c or g.
<220> FEATURE:
<221> NAME/KEY: misc_feature
<222> LOCATION: (23)..(23)
<223> OTHER INFORMATION: Where n=a,t, c or g.
<220> FEATURE:
<221> NAME/KEY: misc_feature
<222> LOCATION: (24)..(24)
<223> OTHER INFORMATION: Where n=a,t, c or g.
<220> FEATURE:
<221> NAME/KEY: misc_feature
<222> LOCATION: (97)..(97)
<223> OTHER INFORMATION: Where n=a,t, c or g.
<220> FEATURE:
<221> NAME/KEY: misc_feature
<222> LOCATION: (98)..(98)
<223> OTHER INFORMATION: Where n=a,t, c or g.
<220> FEATURE:
<221> NAME/KEY: misc_feature
<222> LOCATION: (99)..(99)
<223> OTHER INFORMATION: Where n=a,t, c or g.

<400> SEQUENCE: 8
tccccatgca agcgatgcac gnnngactcg tccgaccccg cttctcccgc ctacatcatt    60
ccccgaccag gtggcgaagt catctgcggc gggacgnnng gcgtgggaga ctgggacttg   120

<210> SEQ ID NO 9
<211> LENGTH: 120
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: Where n=a,t, c or g.
<220> FEATURE:
<221> NAME/KEY: misc_feature
<222> LOCATION: (23)..(23)
<223> OTHER INFORMATION: Where n=a,t, c or g.
<220> FEATURE:
<221> NAME/KEY: misc_feature
<222> LOCATION: (24)..(24)
<223> OTHER INFORMATION: Where n=a,t, c or g.
<220> FEATURE:
<221> NAME/KEY: misc_feature
<222> LOCATION: (97)..(97)
<223> OTHER INFORMATION: Where n=a,t, c or g.
<220> FEATURE:
<221> NAME/KEY: misc_feature
<222> LOCATION: (98)..(98)
<223> OTHER INFORMATION: Where n=a,t, c or g.
<220> FEATURE:
<221> NAME/KEY: misc_feature
<222> LOCATION: (99)..(99)
<223> OTHER INFORMATION: Where n=a,t, c or g.

<400> SEQUENCE: 9
caagtcccag tctcccacgc cnnncgtccc gccgcagatg acttcgccac ctggtcgggg    60
aatgatgtag gcgggagaag cggggtcgga cgagtcnnnc gtgcatcgct tgcatgggga   120

<210> SEQ ID NO 10
<211> LENGTH: 7
<212> TYPE: PRT
<213> ORGANISM: Artificial Sequence
<220> FEATURE:
<223> OTHER INFORMATION: Motif

<400> SEQUENCE: 10

Arg Cys Thr Met Asp Ser Ser
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Motif

<400> SEQUENCE: 11

Gly Gly Thr Tyr Gly Val Gly
1               5
```